United States Patent
Ralston et al.

(10) Patent No.: US 10,695,034 B2
(45) Date of Patent: Jun. 30, 2020

(54) AUTONOMOUS ULTRASOUND PROBE AND RELATED APPARATUS AND METHODS

(71) Applicant: Butterfly Network, Inc., Guilford, CT (US)

(72) Inventors: Tyler S. Ralston, Clinton, CT (US); Nevada J. Sanchez, Guilford, CT (US)

(73) Assignee: Butterfly Network, Inc., Guilford, CT (US)

( * ) Notice: Subject to any disclaimer, the term of this patent is extended or adjusted under 35 U.S.C. 154(b) by 0 days.

(21) Appl. No.: 14/714,150

(22) Filed: May 15, 2015

(65) Prior Publication Data
US 2016/0331353 A1    Nov. 17, 2016

(51) Int. Cl.
*A61B 8/00* (2006.01)
*G01S 7/52* (2006.01)
(Continued)

(52) U.S. Cl.
CPC ............ *A61B 8/546* (2013.01); *A61B 8/4444* (2013.01); *A61B 8/56* (2013.01); *G01S 7/52082* (2013.01); *G01S 15/899* (2013.01); *A61B 8/4427* (2013.01); *A61B 8/4477* (2013.01); *A61B 8/485* (2013.01); *A61B 8/488* (2013.01); *A61B 8/5207* (2013.01); *A61B 8/5276* (2013.01); *G01S 7/5205* (2013.01);
(Continued)

(58) Field of Classification Search
CPC ............ G01S 7/52038; G01S 7/52039; G01S 7/52041; G01S 7/52046; G01S 7/52073; A61B 8/4427; A61B 8/4416; A61B 8/4254; A61B 8/4411; A61B 5/7207–7214; A61B 8/00; A61B 8/585; A61B 8/5276; A61B 5/11; A61B 8/465
See application file for complete search history.

(56) References Cited

U.S. PATENT DOCUMENTS 5,269,307 A    12/1993  Fife et al.
5,740,805 A     4/1998  Dolazza et al.
(Continued)

FOREIGN PATENT DOCUMENTS

CN    101163987 A    4/2008
TW    M444152 U      1/2013
(Continued)

OTHER PUBLICATIONS

Agarwal et al., Single-Chip Solution for Ultrasound Imaging Systems: Initial Results. 2007 IEEE Ultrasonics Symposium. Oct. 1, 2007;1563-6.
(Continued)

*Primary Examiner* — Angela M Hoffa
*Assistant Examiner* — Helene Bor
(74) *Attorney, Agent, or Firm* — Wolf, Greenfield & Sacks, P.C.

(57) ABSTRACT

An ultrasound apparatus comprising a plurality of ultrasonic transducers, a non-acoustic sensor, a memory circuitry to store control data for operating the ultrasound apparatus to perform an acquisition task, and a controller. The controller is configured to receive an indication to perform the acquisition task, receive non-acoustic data obtained by the non-acoustic sensor, and control, based on the control data and the non-acoustic data, the plurality of ultrasonic transducers to obtain acoustic data for the acquisition task.

30 Claims, 9 Drawing Sheets

(51) Int. Cl.
*G01S 15/89* (2006.01)
*A61B 8/08* (2006.01)

(52) U.S. Cl.
CPC ....... *G01S 7/52019* (2013.01); *G01S 7/52096* (2013.01); *G01S 15/8961* (2013.01); *G01S 15/8963* (2013.01)

(56) References Cited

U.S. PATENT DOCUMENTS

| | | | |
|---|---|---|---|
| 5,873,830 A * | 2/1999 | Hossack | G01S 7/52046 |
| | | | 600/447 |
| 5,957,846 A * | 9/1999 | Chiang | A61B 8/4236 |
| | | | 600/447 |
| 6,524,244 B1 | 2/2003 | Knell et al. | |
| 6,540,682 B1 * | 4/2003 | Leavitt | A61B 8/4427 |
| | | | 600/443 |
| 6,880,137 B1 | 4/2005 | Burlison et al. | |
| 7,030,536 B2 | 4/2006 | Smith et al. | |
| 7,115,093 B2 * | 10/2006 | Halmann | A61B 8/14 |
| | | | 600/437 |
| 7,549,961 B1 | 6/2009 | Hwang | |
| 8,852,103 B2 | 10/2014 | Rothberg et al. | |
| 2003/0097071 A1 | 5/2003 | Halmann et al. | |
| 2003/0114760 A1 | 6/2003 | Robinson | |
| 2005/0121734 A1 * | 6/2005 | Degertekin | A61B 5/0215 |
| | | | 257/414 |
| 2005/0171431 A1 | 8/2005 | Petersen | |
| 2005/0219096 A1 * | 10/2005 | Freeman | G01S 7/52028 |
| | | | 341/143 |
| 2005/0228284 A1 * | 10/2005 | Baumgartner | A61B 5/6844 |
| | | | 600/459 |
| 2005/0240127 A1 | 10/2005 | Seip et al. | |
| 2007/0083119 A1 * | 4/2007 | Adachi | A61B 8/12 |
| | | | 600/437 |
| 2007/0239019 A1 | 10/2007 | Richard et al. | |
| 2007/0242567 A1 | 10/2007 | Daft et al. | |
| 2007/0276238 A1 | 11/2007 | Sudol | |
| 2008/0194951 A1 * | 8/2008 | Poland | A61B 8/00 |
| | | | 600/437 |
| 2009/0142872 A1 | 6/2009 | Park et al. | |
| 2009/0250729 A1 | 10/2009 | Lemmerhirt et al. | |
| 2009/0306509 A1 * | 12/2009 | Pedersen | G01S 15/8936 |
| | | | 600/446 |
| 2010/0016744 A1 * | 1/2010 | Brost | A61B 8/02 |
| | | | 600/511 |
| 2010/0063397 A1 | 3/2010 | Wagner | |
| 2010/0152587 A1 | 6/2010 | Haider et al. | |
| 2010/0191894 A1 | 7/2010 | Bartley et al. | |
| 2010/0256488 A1 | 10/2010 | Kim et al. | |
| 2010/0317972 A1 | 12/2010 | Baumgartner et al. | |
| 2011/0055447 A1 | 3/2011 | Costa | |
| 2011/0071397 A1 | 3/2011 | Wodnicki et al. | |
| 2011/0077526 A1 * | 3/2011 | Zwirn | A61B 5/0095 |
| | | | 600/459 |
| 2011/0218436 A1 | 9/2011 | Dewey et al. | |
| 2012/0022379 A1 | 1/2012 | Gubbini et al. | |
| 2012/0059243 A1 * | 3/2012 | Vortman | A61N 7/02 |
| | | | 600/411 |
| 2012/0238875 A1 * | 9/2012 | Savitsky | A61B 8/4254 |
| | | | 600/443 |
| 2013/0053697 A1 * | 2/2013 | Holl | A61B 8/54 |
| | | | 600/459 |
| 2013/0116561 A1 | 5/2013 | Rothberg et al. | |
| 2014/0288428 A1 | 3/2014 | Rothberg et al. | |
| 2015/0032002 A1 | 1/2015 | Rothberg et al. | |

FOREIGN PATENT DOCUMENTS

| | | |
|---|---|---|
| WO | WO 2007/096636 A1 | 8/2007 |
| WO | WO 2009/135255 A1 | 11/2009 |
| WO | WO 2014/136030 A1 | 9/2014 |
| WO | WO 2014/151362 A2 | 9/2014 |

OTHER PUBLICATIONS

Cheng et al., CMUT-in-CMOS ultrasonic transducer arrays with on-chip electronics. Transducers 2009. IEEE. Jun. 21, 2009;1222-5.
Daft et al., 5F-3 A Matrix Transducer Design with Improved Image Quality and Acquisition Rate. 2007 IEEE Ultrasonics Symposium. Oct. 1, 2007;411-5.
Daft et al., Microfabricated Ultrasonic Transducers Monolithically Integrated with High Voltage Electronics. 2004 IEEE Ultrasonics Symposium. Aug. 23, 2004;1:493-6.
Doody et al., Modeling and Characterization of CMOS-Fabricated Capacitive Micromachined Ultrasound Transducers. J Microelectromechan Sys. Feb. 2011;20(1):104-118.
International Search Report and Written Opinion for Application No. PCT/US2016/032261 dated Jun. 9, 2016.
International Search Report and Written Opinion dated Nov. 13, 2014 for Application No. PCT/US2014/032803.
Herper, An Entrepreneur Aims to Peer Inside the Body With a Small, Simple, Cheap Device. Forbes. https://www.forbes.com/sites/matthewherper/2017/10/27/an-entrepreneur-aims-to-peer-inside-the-body-with-a-small-simple-cheap-device/#5bb9ea6f5e5a dated Oct. 27, 2017. Last accessed Nov. 8, 2017. 4 pages.
Regalado, This Doctor Diagnosed His Own Cancer with an iPhone Ultrasound. MIT Technology Review. haps://www.technologyreview.com/s/609195/this-doctor-diagnosed-his-own-cancer-with-an-iphone-ultrasound/ Dated Oct. 27, 2017. Last accessed Nov. 8, 2017. 9 pages.
EP 16796988.0, Jan. 4, 2019, Extended European Search Report.
Taiwanese Communication for Taiwanese Application No. 105114870 dated Jan. 19, 2018.
Extended European Search Report dated Jan. 4, 2019 in connection with European Application No. EP 16796988.0.

* cited by examiner ic # AUTONOMOUS ULTRASOUND PROBE AND RELATED APPARATUS AND METHODS

BACKGROUND

1. Field

The present application relates to an architecture and methods for controlling a programmable ultrasound probe.

2. Related Art

Ultrasound imaging systems typically include an ultrasound probe connected to a host by an analog cable. The ultrasound probe is controlled by the host to emit and receive ultrasound signals. The received ultrasound signals are processed to generate an ultrasound image.

SUMMARY

Aspects of the present application relate to an ultrasound probe configured to autonomously perform an acquisition task comprising a sequence of one or multiple ultrasound acquisitions, corresponding to an imaging mode, in response to an initiation command received from a device external to the ultrasound probe. The ultrasound probe may include memory for storing control data used to govern operation of the ultrasound probe as it performs the acquisition task. The ultrasound probe may also include programmable circuitry, and the control data may include all the parameters required to configure (e.g., program) the programmable circuitry to operate in order to perform the sequence of ultrasound acquisitions. For example, the control data associated with a particular imaging mode may include one or more parameter values for configuring programmable ultrasound circuitry (e.g., circuitry governing transmit and receive functionality of the ultrasound probe) to perform the sequence of ultrasound acquisitions associated with the particular imaging mode and/or one or more timing values indicating when various ultrasound circuitry components are to operate as imaging is performed. The control data stored in the memory may include all the parameter and timing values needed to operate the ultrasound probe to perform the sequence of acquisitions for the acquisition task. In this way, the ultrasound probe may perform the sequence of acquisitions autonomously in response to a simple command that causes the ultrasound probe to begin the sequence of acquisitions (e.g., in response to receipt of a memory address pointing to the control data used to perform the sequence of acquisitions).

According to an aspect of the present application an ultrasound apparatus is provided. The ultrasound apparatus comprises a plurality of ultrasonic transducers, a non-acoustic sensor, a memory circuitry to store control data for operating the ultrasound apparatus to perform an acquisition task, and a controller. The controller is configured to receive an indication to perform the acquisition task, receive non-acoustic data obtained by the non-acoustic sensor, and control, based on the control data and the non-acoustic data, the plurality of ultrasonic transducers to obtain acoustic data for the acquisition task.

According to an aspect of the present application a computer-readable storage device is provided. The computer-readable storage device stores instructions that, when executed by an ultrasound apparatus comprising a plurality of ultrasonic transducers, a non-acoustic sensor, and a memory circuitry configured to store control data for operating the ultrasound apparatus to perform an acquisition task, cause the ultrasound apparatus to perform a process. The process comprises receiving an indication to perform the acquisition task, receiving non-acoustic data obtained by the non-acoustic sensor, and controlling, based on the control data and the non-acoustic data, the plurality of ultrasonic transducers to obtain acoustic data for the acquisition task.

BRIEF DESCRIPTION OF DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

DETAILED DESCRIPTION

Figure 1:
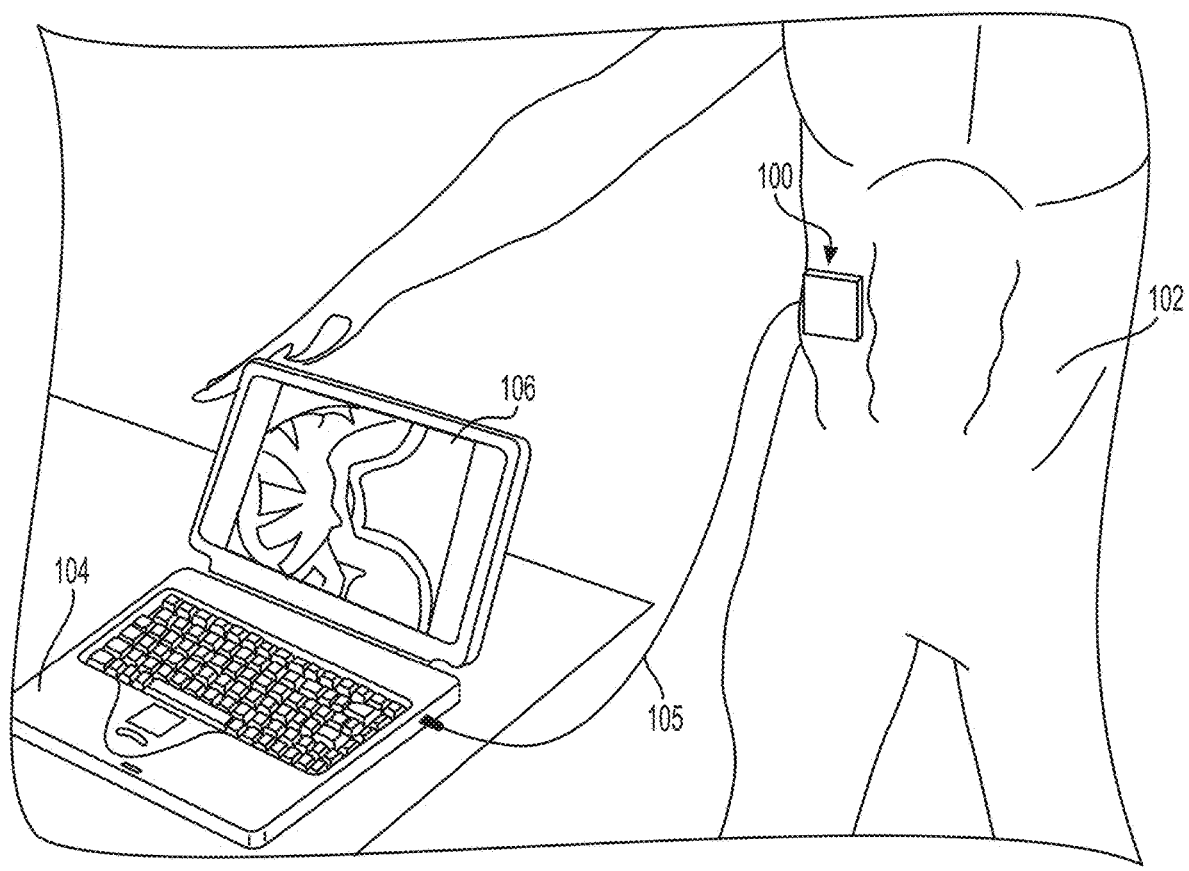
FIG. 1 illustrates an example of an ultrasound probe configured to perform a sequence of acquisitions autonomously in response to an initiation command provided by a device external to the ultrasound probe, in accordance with some embodiments of the technology described herein.

In conventional ultrasound systems, the ultrasound probe must be in continuous communication with a host computer to perform ultrasound imaging. In some ultrasound systems, this is because the host includes most, if not all, control, transmit, and receive circuitry, or at least some of these components, and must provide the "dummy" ultrasound probe with multiple commands and parameters in order to perform even a single acquisition. Even more communication between the host and probe is required when performing imaging in an ultrasound imaging mode that constitutes a sequence of multiple acquisitions. As a result of the need for constant communication between the host and the probe during imaging, conventional ultrasound systems are complex (e.g., complex and costly analog cables are typically used to connect conventional ultrasound probes) and are not modular because the ultrasound probes require hosts specifically programmed to control the probes and cannot simply be plugged into any host such as a laptop computer or a personal digital assistant.

The inventors have recognized that ultrasound systems may be improved if ultrasound probes could operate largely independently from their host, requiring minimal communication. Aspects of the autonomous ultrasound probes described herein provide the benefits of decreased complexity of host devices in ultrasound systems as well as decreased complexity of the connections between the host devices and the ultrasound probes (e.g., relatively simple digital connections may be used), increased modularity because autonomous ultrasound probes, in accordance with embodiments described herein, may be coupled to a variety of hosts, and more efficient operation (e.g., by reducing the amount of communication overhead between host devices and probes during imaging). Generally, aspects of the autonomous ultrasound probes described herein increase accessibility of ultrasound technology beyond that afforded by the relatively complex and costly conventional ultrasound systems.

Accordingly, certain aspects of the technology described herein are directed to an ultrasound probe that is programmable to perform imaging, autonomously, in one or multiple ultrasound imaging modes. Upon being triggered to start imaging in a selected ultrasound imaging mode, the ultrasound probe may perform imaging in the selected imaging mode without receiving additional control information (e.g., commands, parameters, etc.) from any external source in furtherance of performing the imaging. For example, the ultrasound probe may receive a request from a host device external to the probe that causes the probe to initiate imaging in a desired imaging mode and, in response, the probe may perform imaging in the desired imaging mode (e.g., by performing a sequence of multiple acquisitions associated with the imaging mode) without receiving, from the host device, any further information or instructions for controlling the way in which the probe performs the requested imaging. As such, in response to an indication (e.g., a code, a function call, a pointer, etc.) to begin imaging in a desired mode, an autonomous ultrasound probe may begin and complete imaging in the particular mode using only control data stored on the probe and without using any external control information, aside from the indication to begin the imaging, that is not stored on the probe.

In some embodiments, performing imaging in a particular ultrasound imaging mode may comprise performing an acquisition task comprising a sequence of multiple acquisitions (of a same type and/or of a different type) associated with the particular ultrasound imaging mode. The ultrasound probe may autonomously perform imaging in the particular ultrasound imaging mode by autonomously performing the acquisition task. For example, the ultrasound probe may receive an indication from a host external to the probe to start imaging in a selected mode and, in response to receiving the indication, may perform the sequence of multiple acquisitions associated with the selected mode without using additional control data from the host. The ultrasound probe may be configured to access, based on the indication, control data stored in memory of the ultrasound probe and use the accessed control data to perform the sequence of acquisitions for the selected imaging mode.

In some embodiments, an ultrasound probe may be configured to autonomously perform imaging in any suitable imaging mode(s) for which the ultrasound probe stores control data that governs the way in which the ultrasound probe operates when performing the sequence of acquisitions associated with the imaging mode(s). For example, an ultrasound probe may be configured (e.g., programmed to) perform autonomous imaging in any one or more of the following imaging modes: A-mode imaging, B-mode imaging, C-mode imaging, M-mode imaging, pulse inversion imaging, harmonic imaging, imaging with background subtraction, moving indicator imaging, linear frequency modulated imaging, non-linear frequency modulated imaging, coded excitation imaging, coded aperture imaging, cross-sectional imaging, en face imaging (e.g., which may involve generating an image of a region in the subject that is substantially parallel to the surface of the probe), Doppler imaging (e.g., pulsed wave Doppler imaging, continuous wave Doppler imaging, color Doppler imaging, power Doppler imaging, any combination of the above-listed Doppler imaging modes, etc.), perturbation imaging (e.g., shearwave imaging), compounded imaging (e.g., frequency-compounded imaging, angle-compounded imaging, etc.), sensor-dependent imaging modes in which the manner in which the ultrasound probe performs imaging depends on measurements obtained by one or more sensors onboard the probe during imaging, and/or any suitable combination of the above-listed or other modes. As discussed in more detail below, many of the above-listed imaging modes are associated with respective sequences of acquisitions so that performing imaging in one such mode requires performing a sequence of acquisitions associated with the mode. It should be appreciated that the above list of imaging modes is illustrative and non-limiting, as an ultrasound probe, according to aspects of the technology described herein, may be configured to perform imaging in any one or more other imaging modes in addition to or instead of the above-listed imaging modes.

In some embodiments, an ultrasound probe includes memory circuitry which stores control data used for controlling the ultrasound probe to perform imaging in any suitable imaging mode(s) (e.g., in any one or more of the above-listed imaging modes). "Memory circuitry" as used herein may alternatively be referred to simply as "memory" in some embodiments. The memory may store control data governing operation of the probe in performing imaging in one or more imaging modes each of which may be associated with a respective sequence of multiple acquisitions. Control data governing operation of the ultrasound probe in performing imaging in an imaging mode associated with a respective sequence of acquisitions may comprise data for controlling the ultrasound probe to perform each acquisition in the sequence. For example, an imaging mode (e.g., harmonic imaging mode) may comprise performing one acquisition of a first type (e.g., an acquisition using a particular pulse) followed by another acquisition of a second type (e.g., an acquisition using the particular pulse, but phase shifted by 180 degrees). The ultrasound probe may store control data comprising first control data for controlling the ultrasound probe to perform the acquisition of the first type and second control data for controlling the ultrasound probe to perform the acquisition of the second type. In this way, the ultrasound probe may receive an indication to perform imaging in a mode associated with a sequence of multiple acquisitions (e.g., an indication to perform harmonic imaging) and perform each of the acquisitions in the sequence by using control data stored on the probe without receiving any additional control information from any device external to the probe.

The control data may also comprise any suitable data for controlling the ultrasound probe to perform an acquisition or a sequence of acquisitions. For example, an ultrasound probe may include programmable circuitry (e.g., control, transmit, and/or receive circuitry) and the control data may, in some embodiments, include all the information required to configure (e.g., program) the programmable circuitry to operate in order to perform each of one or more acquisitions. For example, the control data may include all the parameter values for configuring the probe's programmable circuitry to perform a particular type of ultrasound acquisition and timing values indicating when various programmable circuitry components are to operate (e.g., relative to one another) in order for the ultrasound probe to perform the particular type of acquisition. As another example, the control data may include timing values indicating when the ultrasound probe is to perform the acquisitions in a sequence of acquisitions relative to one another.

In some embodiments, one or more parameter values and/or timing values used for governing operation of the ultrasound probe may be computed based, at least in part, on the control data stored on the ultrasound probe. For example, one or more parameter values and/or timing values for controlling operation of ultrasonic transducers may be derived from parameter values stored in the control data by using delay mesh circuitry of the ultrasound probe. As another example, one or more parameter values and/or timing values for controlling operation of the ultrasound transducers may be modified based, at least in part, on non-acoustic data obtained by a non-acoustic sensor onboard the ultrasound probe.

In some embodiments, an ultrasound probe may include an acquisition controller that is configured to control operation of the probe in one or more imaging modes using control data stored in the probe's memory. For example, the acquisition controller may receive an indication to perform imaging in a particular imaging mode, access control data associated with the particular imaging mode, and control the probe to operate in accordance with the accessed control data. The control data may comprise parameter values and timing values for controlling operation of the probe's programmable circuitry (e.g., parameter values for transmit circuitry, parameter values for receive circuitry, timing values for transmit circuitry, timing values for receive circuitry, etc.), and the acquisition controller may control the probe to operate in accordance with the accessed control data by controlling programmable circuitry components in accordance with respective parameter and timing values.

In some embodiments, for example, an ultrasound probe may comprise memory storing control data governing a first type of acquisition and an acquisition controller configured to control the probe's programmable circuitry by using the control data. The control data may include parameter data and timing data for the first type of acquisition such as, for example, parameter values and timing values for operating the probe's transmit circuitry and receive circuitry during the first type of acquisition, and the acquisition controller may control the probe's operation during the first type of acquisition based, at least in part, on the parameter values and timing values. As one non-limiting example, the control data may comprise one or more transmit timing values indicating when one or more components of the transmit circuitry are to operate (e.g., a transmit timing value indicating when a pulser is to operate, a transmit timing value indicating when a waveform generator is to operate, a transmit timing value indicating when a delay unit is to operate, etc.), and the acquisition controller may be configured to control the transmit circuitry in accordance with the transmit timing value(s). As another non-limiting example, the control data may comprise one or more transmit parameter values indicating how one or more components of the transmit circuitry are to operate during the first type of acquisition (e.g., one or more transmit parameter values indicating a type of waveform to be generated by a waveform generator, one or more transmit parameter values indicating how a delay unit is to operate, one or more transmit parameter values indicating how a pulser is to operate), and the acquisition controller may be configured to control the transmit circuitry in accordance with the transmit parameter values. As another non-limiting example, the control data may comprise one or more receive timing values indicating when one or more components of the receive circuitry are to operate (e.g., a receive timing value indicating when analog receive circuitry is to operate, a receive timing value indicating when an analog-to-digital converter (ADC) is to operate, a receive timing value indicating when digital receive circuitry is to operate, etc.), and the acquisition controller may be configured to control the receive circuitry in accordance with the receive timing value(s). As another non-limiting example, the control data may comprise one or more receive parameter values indicating how one or more components of the receive circuitry are to operate during the first type of acquisition, and the acquisition controller may be configured to control the receive circuitry in accordance with the receive parameter values.

In some embodiments, the ultrasound probe is an ultrasound on a chip probe incorporating one or more of the aspects described above. The ultrasound probe may include ultrasonic transducers and programmable circuitry, such as programmable control, transmit, and/or receive circuitry. The programmable circuitry of the ultrasound probe may be included on the same substrate as the ultrasonic transducers in some embodiments, or on one or more separate substrates in alternative embodiments.

Aspects of the present application relate to manufacturing ultrasound probes and circuitry of the types describes herein. For example, manufacturing an ultrasound probe may comprise forming a memory on the ultrasound probe for storing control data that governs operation of the ultrasound probe in performing imaging in one or more imaging modes. Manufacturing an ultrasound probe may further comprise forming control circuitry (e.g., an acquisition controller and other control circuitry described with respect to FIG. 4 below) that controls ultrasound probe circuitry (e.g., transmit and/or receive circuitry described with respect to FIGS. 5, 6A, and 6B below) to perform imaging in accordance with the control data. The memory and the control circuitry may be formed on a same substrate as a plurality of ultrasonic transducers of the ultrasound probe, or may be formed on one or more separate substrates in alternative embodiments.

The aspects and embodiments described above, as well as additional aspects and embodiments, are described further below. These aspects and/or embodiments may be used individually, all together, or in any combination of two or more, as the application is not limited in this respect.

To provide context and facilitate explanation of the various aspects of the present application, a specific example of an ultrasound probe is now described together with specific examples of programmable circuitry that may be included in such a probe. Yet, it should be appreciated that aspects of the present application apply more broadly than the specific ultrasound probe and programmable circuitry now described.

FIG. 1 illustrates an example of an ultrasound probe 100 configured to autonomously perform imaging in a desired imaging mode in response to receiving an indication to begin imaging in the desired imaging mode. The ultrasound probe 100 is shown for purposes of illustration as being used to investigate a subject 102. As illustrated in the embodiment of FIG. 1, ultrasound probe is coupled to host device 104 via a connection 105. The host device 104 may provide an initiation command to the ultrasound probe 100 to begin imaging in a desired imaging mode (e.g., in any of the imaging modes described herein), and in response to receiving the initiation command, ultrasound probe 100 may commence imaging in the desired imaging mode using control data stored in the ultrasound probe's memory (not shown in FIG. 1).

The host device 104 may be any suitable computing device and may be a portable computing device (e.g., a laptop, smartphone, a tablet, a personal digital assistant, a computing device affixed to portable medical equipment, etc.) or a fixed computing device (e.g., a desktop computer, a rack mount computer, a computing device affixed to other fixed medical equipment, etc.). In the illustrated embodiment, host device 104 includes display screen 106 on which ultrasound images may be displayed in real time, substantially in real time as imaging is performed (e.g., within a threshold number of frames such as within one, five or ten frames, within a threshold amount of time such as within one, five, or ten seconds, etc.), or after imaging is performed, though in other embodiments host device 104 may not have a display screen.

In the embodiment illustrated in FIG. 1, connection 105 is a wired connection, but may be a wireless connection (e.g., a Bluetooth® connection or near field communication (NFC)), as aspects of the technology described herein are not limited in this respect. The connection 105 may be a digital connection, for example being of a type commonly used with commercial digital electronics, such as a universal serial bus (USB) cable, Thunderbolt, or FireWire. Connection 105 may connect to the serial output port 314 and clock input port 316 of the ultrasound probe 100 (shown in FIG. 3).

Figure 2A:
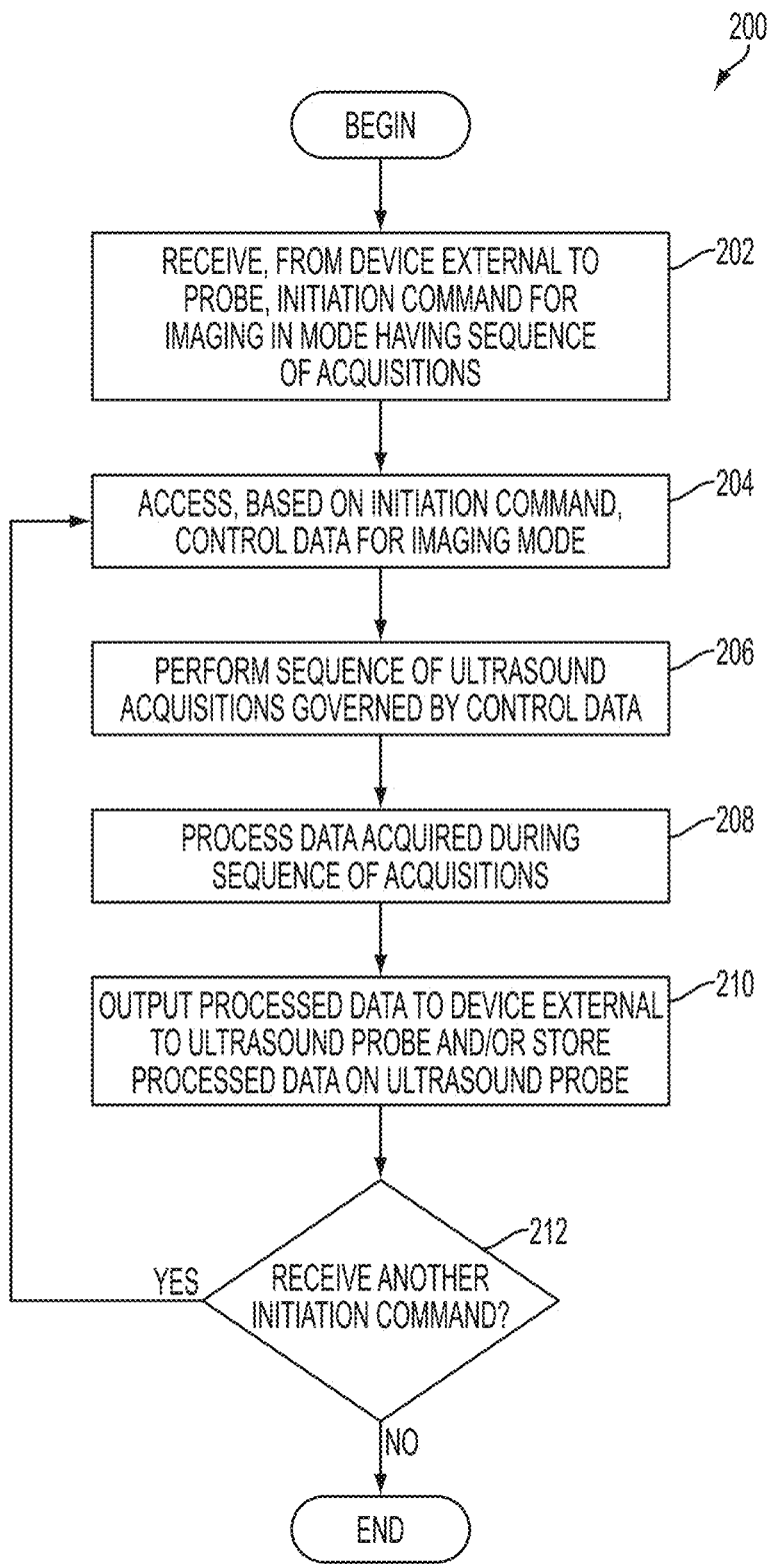
FIG. 2A is a flowchart of an illustrative process for using an ultrasound probe to perform, in response to an initiation command received from a device external to the probe, a sequence of acquisitions governed by control data stored on the ultrasound probe, in accordance with some embodiments of the technology described herein.

FIG. 2A is a flowchart of illustrative process 200 for using an ultrasound probe to perform, in response to an initiation command received from a device external to the probe, a sequence of acquisitions governed by control data stored on the ultrasound probe. Process 200 may be performed by any suitable ultrasound probe of the types described herein and, for example, may be performed by ultrasound probe 100 described with reference to FIGS. 1 and 3.

Process 200 begins at act 202, when the ultrasound probe receives an initiation command for performing imaging in a particular imaging mode from a device external to the ultrasound probe (e.g., from host device 104 described with reference to FIG. 1). The particular imaging mode may be associated with a sequence of acquisitions such that imaging in the particular imaging mode comprises performing the associated sequence of acquisitions. Examples of imaging modes and associated sequences of acquisitions are provided herein.

The initiation command may be any suitable indication to begin performing an acquisition task imaging. In some embodiments, the initiation command may identify, directly or indirectly, a particular imaging mode. For example, the ultrasound probe may be configured to operate in multiple imaging modes and the initiation command may select the particular imaging mode, or modes, for use in a particular instance. For example, the initiation command may be a function call, a pointer (e.g., a memory address), a code, a keyword, and/or any other suitable indication that causes the ultrasound probe to begin imaging in a particular imaging mode, or modes, as aspects of the technology described herein are not limited by the type of initiation command used. In some embodiments, the initiation command may instruct the ultrasound probe to begin imaging and the ultrasound probe may select the particular imaging mode, or modes, on its own or using other data received by the ultrasound probe (e.g., using data from one or more sensors indicative of appropriate imaging mode(s)). The initiation command in at least some embodiments does not include any control data that governs operation of the ultrasound probe for performing imaging in the particular imaging mode. Thus, for example, the initiation command in at least some embodiments does not include parameter values and/or timing values for performing any of the acquisitions associated with an imaging mode. In some embodiments, all of the control data including parameter values and/or timing values is stored by the ultrasound probe prior to receipt of the initiation command.

After receiving the initiation command, the ultrasound probe accesses, based on the initiation command, control data governing operation of the ultrasound probe in the particular imaging mode. The control data may be stored in memory of the ultrasound probe (e.g., in sequence memory 402, timing memory 404, and parameter memory 406 described with reference to FIG. 4). The control data for controlling operation of the probe in the particular imaging mode (and/or one or more other modes) may have been loaded onto the ultrasound probe prior to beginning of the execution of the process 200. The ultrasound probe may access control data for the particular imaging mode based on the initiation command in any suitable way. For example, the initiation command may specify one or more memory locations (e.g., one or more memory addresses) in the probe's memory at which the control data is stored (e.g., the initiation command may specify a starting memory address for the region of memory in which the control data is stored). As another example, the probe may map the initiation command to one or more memory locations (e.g., using a table, a hashing function, etc.) in the probe's onboard memory at which the control data is stored. The ultrasound probe may use the initiation command to access the control data for the particular imaging mode in any other suitable way, as aspects of the technology described herein are not limited in this respect.

Next, process 200 proceeds to act 206, where the ultrasound probe performs a sequence of ultrasound acquisitions (for the particular imaging mode) in accordance with the control data accessed at act 204. For example, the control data may comprise parameter values and timing values for various onboard circuitry (e.g., transmit circuitry, receive circuitry, control circuitry, etc.) of the ultrasound probe and, at act 206, the ultrasound probe may perform the sequence of acquisitions by operating its circuitry in accordance with the parameter values and timing values in the accessed control data. The sequence of acquisitions may comprise one or multiple acquisitions, which depending on the imaging mode, may be, for example, at least two acquisitions, at least 5 acquisitions, at least 10 acquisitions, at least 100 acquisitions, at least 500 acquisitions, and between 10 and 1000 acquisitions. Accordingly, in some embodiments, an ultrasound probe may store control data for performing a sequence of multiple acquisitions (including, in some instances, different types of acquisitions requiring different parameter and/or timing values) such that the probe may autonomously perform the entire sequence of multiple acquisitions in response to a single initiation command in contrast to conventional ultrasound systems in which a host provides one or more commands to an ultrasound probe for performing a single acquisition.

Next, process 200 proceeds to act 208, where the data obtained during the sequence of acquisitions performed at act 206 is processed. The acquired data may be processed in any suitable way. For example, data acquired during a particular acquisition may be filtered (e.g., low-pass filter, band-pass filter, high-pass filter, causal filter, non-causal filter, and/or any other suitable filter), resampled (e.g., downsampled or upsampled), demodulated, denoised, and/or processed in any other suitable way by circuitry onboard the ultrasound probe performing process 200.

In some embodiments, data acquired during one acquisition in the sequence of acquisitions performed at act 206 may be processed without using any data obtained during one or more other acquisitions in the sequence. Alternatively, data acquired during one acquisition in the sequence of acquisitions performed at act 206 may be processed by using data obtained during one or more other acquisitions in the sequence. For example, data acquired in one acquisition in the sequence may be added to or subtracted from data acquired in another acquisition (e.g., the next acquisition) in the sequence. Such processing may be used in various imaging modes including, but not limited to, harmonic imaging, moving indicator imaging, and background imaging, as described in more detail below. As another example, data acquired in one acquisition may be filtered at least in part by using data obtained in one or more other acquisitions in the sequence (e.g., by using a filter formed based at least in part on the data obtained in one or more other acquisitions in the sequence).

Next, process 200 proceeds to act 210, where the processed data obtained at act 208 is output to a device external to the probe (e.g., output to host device 104 via connection 105, previously described with reference to FIG. 1). In some embodiments, at least a portion (e.g., all) of the processed data may be output to an external device and none of it saved on the probe. In other embodiments, at least a portion of the processed data may be stored on the probe and none of it output to the external device. In yet other embodiments, at least a first portion of the acquired data may be stored on the probe and at least a second portion of the acquired data (which may be the same as or different from the first portion of acquired data) may be output to the external device. Data output from the ultrasound probe to the host device may be used in any suitable way and, for example, may be used to form one or more ultrasound images.

It should be appreciated that, in some embodiments, the ultrasound probe performing process 200 may be configured to perform acts 204, 206, 208, and 210 in response to an initiation command received at act 202, without any further input from the external device that provided the initiation command to the probe. As such, the ultrasound probe may perform acts 204, 206, 208, and 210 independently from the external device. In this way, in response to receiving an initiation command to begin imaging in a particular imaging mode, the ultrasound probe may begin and complete performing the sequence of acquisitions associated with the particular imaging mode before receiving any other information (e.g., control information) from the external device.

After the ultrasound probe completes performance of imaging (during acts 204, 206, 208, and 210) triggered by the initiation command received at act 202, process 200 proceeds to decision block 212, where it is determined whether another initiation command has been received from the external device. When it is determined that another initiation command has been received, process 200 returns, via the YES branch, to act 204 of process 200, and acts 204, 206, 208 and 210 are repeated. Thus, the process 200 may be iterative. It should be appreciated that in instances where the probe receives multiple initiation commands, the probe may not receive any other commands between the initiation commands since the probe may be configured to perform imaging (in response to each of these commands) autonomously. When it is determined, at decision block 212, that another initiation command has not been received, process 200 completes.

It should be appreciated that process 200 is illustrative and that there are variations of process 200. For example, although in the illustrated embodiment of FIG. 2A, an ultrasound probe receives an initiation command to begin imaging in a desired imaging mode from a device external to the ultrasound probe, in other embodiments, the initiation command need not be provided by a device external to the probe and may be provided in another way. For example, the ultrasound probe may include an input device (e.g., a button, a switch, etc.) that may be activated by the probe's user to provide an initiation command to the probe to begin imaging in the desired mode. As another example, the ultrasound probe may include a sensor and the ultrasound probe may begin imaging in a desired mode in response to an event sensed by the sensor (e.g., the ultrasound probe may begin imaging when the sensor determines that the probe is touching a human subject's skin) As another example, although in the illustrated embodiment of FIG. 2A the data acquired during the sequence of acquisitions performed at act 206 is further processed at act 208, in other embodiments the acquired data may not be processed at all and may be output directly to a device external to the probe (e.g., a host device) and/or stored in the probe's memory.

As a further variation on the process 200, in some embodiments not all information is provided to the probe prior to performance of the imaging sequence, such that some information may be provided after the initiation command. For example, the ultrasound probe may begin performing the sequence of acquisitions associated with the particular imaging mode and receive some other control information (e.g., information indicating to continue imaging, information indicating that the external device is operating, information indicating to stop imaging, information indicating to pause imaging, etc.) from the external device before completing performance of the sequence of acquisitions. However, in at least some such embodiments, any such other control information would not provide all of the parameter values and timing values for each of the acquisitions in the sequence of acquisitions associated with the particular imaging mode, because such values would be stored in the probe's memory, as described herein.

Figure 2B:
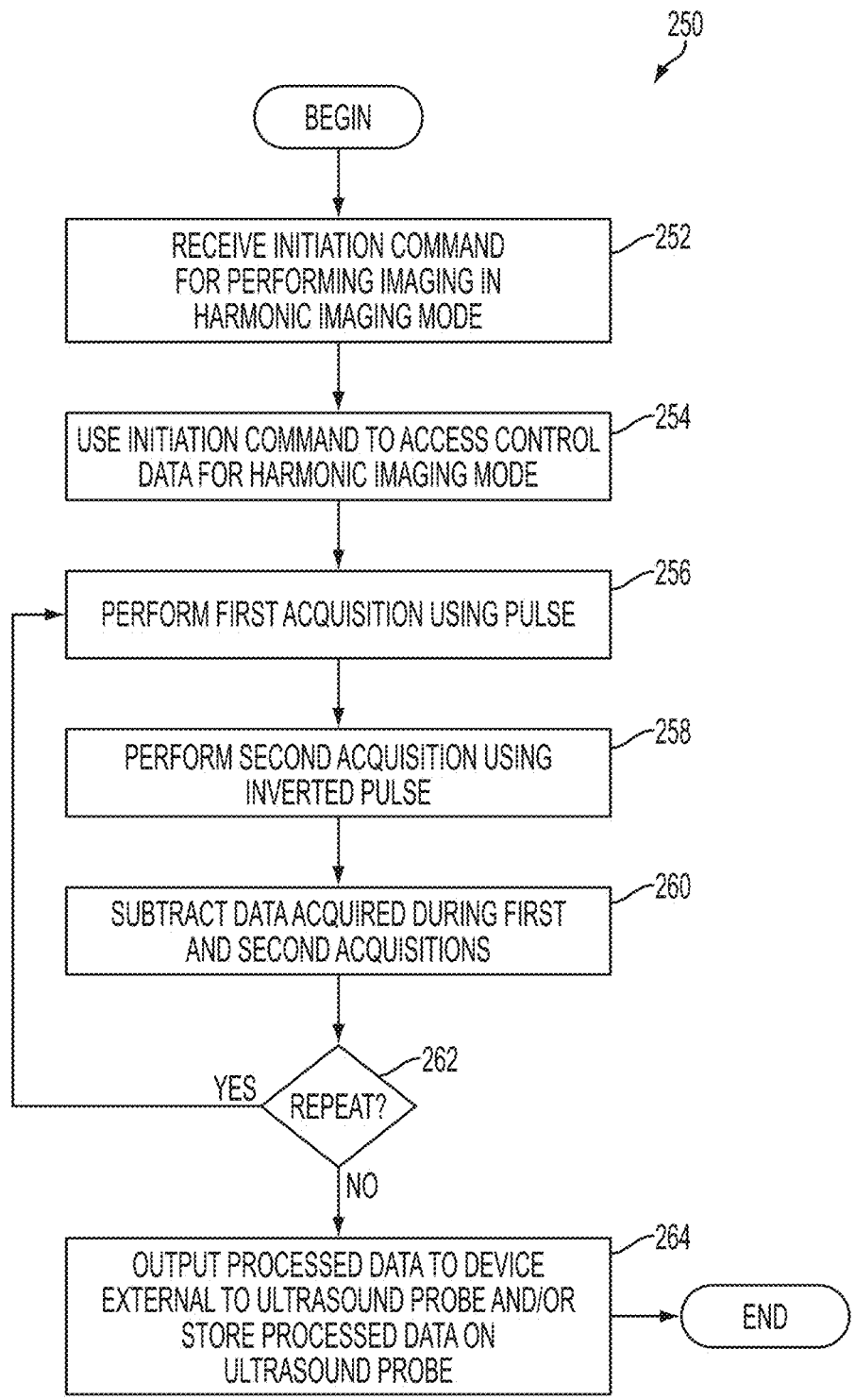
FIG. 2B is a flowchart of an illustrative process for performing harmonic imaging, which is a specific non-limiting example of the process described with respect to FIG. 2A, in accordance with some embodiments of the technology described herein.

FIG. 2B is a flowchart of illustrative process 250 for using an ultrasound probe for performing harmonic imaging and is a non-limiting example of process 200 described with respect to FIG. 2A, in accordance with some embodiments of the technology described herein. Process 250 may be performed by any suitable ultrasound probe of the types described herein and, for example, may be performed by ultrasound probe 100 described with reference to FIGS. 1 and 3.

Process 250 begins at act 252 when an initiation command for performing imaging in a harmonic imaging mode is received. The initiation command may be received from a device external to the probe performing process 250 (e.g., host device 104). The initiation command may be any suitable type of indication to begin imaging in the harmonic imaging mode. Examples of various types of indications are described above with reference to process 200.

Next, process 250 proceeds to act 254, where the ultrasound probe accesses, based on the initiation command, control data governing operation of the ultrasound probe in the harmonic imaging mode. The control data may be stored in the memory of the ultrasound probe and may be accessed in any suitable way, examples of which are described above. As described in more detail below with reference to acts 256, 258, and 260 and decision block 262, the control data may be used to control the probe to perform one or more pairs of acquisitions such that performing one acquisition in a pair comprises using an inverted pulse from the pulse used in performing the other acquisition in the pair.

Next, at acts 256 and 258, the ultrasound probe performs two acquisitions using a pair of inverted pulses. For example, the ultrasound probe may perform a first acquisition using a particular type of pulse (e.g., by emitting the particular type of pulse using one or more of the probe's ultrasonic transducers and receiving one or more ultrasound signals in response to the emitting), at act 256, and then perform a second acquisition using an inverted version of the pulse used during the first acquisition (e.g., the same pulse as in the first acquisition, having a phase shift of 180 degrees), at act 258. The data acquired during this sequence of two acquisitions is then processed, at act 260, whereby the data acquired during the second acquisition is subtracted from the data acquired during the first acquisition. Processing the acquired data in this way emphasizes the response of the subject to harmonics of the fundamental frequency (e.g., one or more multiples of the fundamental frequency) in the processed data.

In some embodiments, the control data accessed at act 254 may control the ultrasound probe to perform a sequence of multiple pairs of acquisitions in order to perform harmonic imaging. Accordingly, after completing the acquisitions of acts 256 and 258, process 250 proceeds to decision block 262, where it is determined whether another pair of acquisitions is to be obtained, which determination may be made automatically based on the control data (e.g., the control data may indicate how many pairs of acquisitions should be performed) or in any other suitable way. When it is determined, at decision block 262, that another pair of acquisitions is to be performed, process 250 returns, via the YES branch, to act 256 and acts 256-260 are repeated. Otherwise, process 250 proceeds to act 262, where all the processed data is output to an external device (e.g., an external host device) and/or stored in the probe's memory.

Although the process 250 illustrated with respect to FIG. 2B relates to imaging in the harmonic imaging mode, it should be appreciated that ultrasound probes in accordance with embodiments described herein may autonomously perform imaging in any suitable image mode(s), examples of which are provided herein. Thus, processes analogous to process 250 may be used for other imaging modes. Also as discussed above, performing imaging in many of the imaging modes described herein comprises performing respective sequences of multiple acquisitions corresponding to the imaging modes.

In some imaging modes, a sequence of acquisitions may comprise multiple acquisitions of a same type, whereby each of multiple acquisitions is performed using the same set of parameters (e.g., in order to obtain multiple measurements of a particular portion of the subject being imaged, for example, to improve the signal to noise ratio or to monitor changes in the portion of the subject).

In some imaging modes, a sequence of acquisitions may comprise different types of acquisitions, whereby one acquisition in the sequence is performed using a different set of parameters than another acquisition in the sequence. For example, in some imaging modes, different acquisitions in the sequence may be used to image different portions of the subject. Accordingly, parameters used to control which portion of the subject the ultrasound probe will image (e.g., parameters that control how to steer the ultrasound wave generated by the probe, the set of ultrasound transducers used to perform imaging, the cross section of the subject being imaged, the depth at which the subject is being imaged, etc.) may vary among acquisitions (e.g., between successive acquisitions) performed by the probe. As another example, in some imaging modes, different types of acquisitions may be used to image the same portion of the subject. For example, to perform harmonic imaging, two different types of acquisitions (a first acquisition using one pulse and a second acquisition using the corresponding inverted pulse) may be used to image the same portion of the subject.

Specific non-limiting examples of imaging modes that may be performed by a probe in response to an initiation command are described below. An ultrasound probe in accordance with embodiments described herein may perform imaging in any of these modes autonomously based on control data stored on the probe. It should be appreciated that an ultrasound probe is not limited to performing imaging in these imaging modes and may be configured to autonomously perform imaging in one or more other imaging modes. It should also be appreciated that an ultrasound probe may perform imaging in a mode that is a combination of two or more of the imaging modes described below and/or other imaging modes.

In some embodiments, an ultrasound probe may be configured to perform imaging in a harmonic imaging mode. As described above with reference to FIG. 2B, in some embodiments, performing imaging in the harmonic imaging mode may comprise performing two-pulse cancellation such that imaging proceeds by performing a sequence of pairs of acquisitions. Each pair of acquisitions in the sequence may include a first acquisition using a particular type of pulse and a second acquisition using an inverted version of the particular type of pulse. The data acquired in the second acquisition may be subtracted from data acquired in the first acquisition to obtain data used for forming a harmonic image. In other embodiments, performing imaging in the harmonic imaging mode may comprise performing three-pulse cancellation such that imaging proceeds by performing a sequence of acquisition triples. For example, each acquisition triple may include a pair of acquisitions using a particular type of pulse and the third acquisition using an inverted version of the particular type of pulse. The third acquisition may have an amount of power equal to the sum of the powers of the other two acquisitions. The data acquired in the third acquisition may be subtracted from the data acquired during the other two acquisitions to obtain data used for forming a harmonic image. An ultrasound probe may be configured to perform harmonic imaging in any other suitable way, as aspects of the technology described herein are not limited in this respect. In the foregoing example, all of the control data for performing harmonic imaging may be stored in memory of the ultrasound probe prior to receipt of an initiation command that initiates imaging. Such control data may include, for example, data indicative of the particular pulse for use in an acquisition, data indicative of an inverted version of the pulse for use in another acquisition, and data indicative of the timing with which one or more components of the ultrasound probe, including transmit circuitry, receive circuitry, and/or waveform generator (s), must be activated (or deactivated as the case may be) in order to effect harmonic imaging.

In some embodiments, an ultrasound probe may be configured to perform imaging in a background subtraction mode. Performing imaging in background subtraction mode may comprise performing a sequence of acquisitions in which one or more acquisitions in the sequence are "passive acquisitions" used to measure background acoustic noise (e.g., the probe may receive without transmitting any pulses prior to performing the receiving) and one or more other acquisitions in the sequence are "active acquisitions" used to image the subject by emitting ultrasound pulses and receiving ultrasound signals generated in response to the emitted ultrasound pulses. The data acquired during the passive acquisitions may be subtracted from data acquired during the active acquisitions to obtain an image in which background acoustic information is removed or at least de-emphasized. An ultrasound probe may be configured to perform background subtraction imaging in any other suitable way, as aspects of the technology described herein are not limited in this respect. In the foregoing example, all of the control data for performing imaging in a background subtraction mode may be stored in memory of the ultrasound probe prior to receipt of an initiation command that initiates imaging. Such control data may include, for example, data indicative of the timing with which one or more components of the ultrasound probe, including transmit circuitry, receive circuitry, and/or waveform generator(s), must be activated (or deactivated as the case may be) in order to effect passive acquisitions and data indicative of the timing with which one or more components of the ultrasound probe must be activated or deactivated in order to effect active acquisitions.

In some embodiments, an ultrasound probe may be configured to perform imaging in moving indicator mode. Performing imaging in moving indicator mode may comprise performing a sequence of multiple acquisitions (e.g., each acquisition in the sequence may be performed in accordance with a same set of parameters in the control data). Subsequently, differences in the data acquired during successive acquisitions may be computed (e.g., by subtracting data obtained in one acquisition from data obtained in a previous acquisition, by using a Wall filter, and/or in any other suitable way) to obtain an indication of what is moving in the subject being imaged. An ultrasound probe may be configured to perform moving indicator imaging in any other suitable way, as aspects of the technology described herein are not limited in this respect. In the foregoing example, all of the control data for performing imaging in a moving indicator mode may be stored in memory of the ultrasound probe prior to receipt of an initiation command that initiates imaging. Such control data may include, for example, data indicative of the timing with which one or more acquisitions are made and data indicative of the timing of such acquisitions.

In some embodiments, an ultrasound probe may be configured to perform imaging in a frequency modulated mode. Performing imaging in a frequency modulated mode may comprise generating pulses using frequency-modulated waveforms (e.g., linear frequency modulated waveforms or non-linear frequency modulated waveforms) and applying a matched filter to the received ultrasound signals (e.g., by correlating the received ultrasound signals with the transmitted ultrasound signal). In this way, an ultrasound probe may be configured to perform pulse compression onboard. An ultrasound probe may be configured to perform frequency modulated imaging in any other suitable way, as aspects of the technology described herein are not limited in this respect. It should be appreciated that frequency modulated imaging may be combined with any other imaging modes described herein for which frequency modulated waveforms may be used. In the foregoing example, all of the control data for performing frequency modulated imaging may be stored in memory of the ultrasound probe prior to receipt of an initiation command that initiates imaging. Such control data may include, for example, data indicative of one or more frequency-modulated waveforms (e.g., linear frequency modulated waveforms or non-linear frequency modulated waveforms) and data indicative of the timing with which one or more components of the ultrasound probe, including transmit circuitry, receive circuitry, and/or waveform generator(s), must be activated or deactivated in order to effect frequency modulated imaging.

In some embodiments, an ultrasound probe may be configured to perform imaging in a coded excitation imaging mode. Performing imaging in a coded excitation imaging mode may comprise performing a sequence of acquisitions in which performing different acquisitions comprises emitting ultrasound pulses generated using different code-excited waveforms. Code-excited waveforms may be formed using any suitable code such as a Golay code or a Barker code or, in some embodiments, may be generated using dithered Gaussian pulses. For example, performing one acquisition in the sequence may comprise emitting ultrasound pulses generated by using a code-excited waveform created based on a first code word in a Golay code, and performing another acquisition in the sequence may comprise emitting ultrasound pulses generated by using another code-excited waveform crated based on a second code word in the Golay code different from the first code word. Matched filtering may be applied to the received ultrasound signals onboard the probe (e.g., by correlating the received ultrasound signals with the transmitted ultrasound signal). An ultrasound probe may be configured to perform coded excitation imaging in any other suitable way, as aspects of the technology described herein are not limited in this respect. In the foregoing example, all of the control data for performing coded excitation imaging may be stored in memory of the ultrasound probe prior to receipt of an initiation command that initiates imaging. Such control data may include, for example, data indicative of multiple code-excited waveforms for generating different ultrasound pulses (e.g., data indicative of Golay or Barker codes or dithered Gaussian pulses) and data indicative of the timing with which one or more components of the ultrasound probe, including transmit circuitry, receive circuitry, and/or waveform generator(s), must be activated or deactivated in order to effect coded excitation imaging.

In some embodiments, an ultrasound probe may be configured to perform imaging in a coded aperture imaging mode. Performing imaging in a coded aperture imaging mode may comprise performing a sequence of acquisitions in which different acquisitions in the sequence comprise inverting the waveforms transmitted by different subsets of the probe's ultrasonic elements. For example, performing one acquisition in the sequence may comprise inverting the waveforms transmitted by a first subset of the ultrasound elements and performing another acquisition in the sequence may comprise inverting the waveforms transmitted by a second subset of the ultrasound elements different from the first subset of ultrasound elements. The subsets of elements for which to invert the transmitted waveforms in a particular acquisition may be selected using a code such as a Hadamard code, for example. Data obtained from the sequence of acquisitions may be processed (e.g., via appropriate sequences of additions and subtractions of data acquired in successive acquisitions for a Hadamard code) to obtain processed data used for forming an image of the subject. An ultrasound probe may be configured to perform coded excitation imaging in any other suitable way, as aspects of the technology described herein are not limited in this respect. For example, in some embodiments, the ultrasound probe may be configured to perform "receive-mode" coded aperture imaging in contrast to the transmit-mode coded aperture imaging described above. In receive-mode aperture imaging, the data acquired during different acquisitions in a sequence of acquisitions may be encoded differently according to a particular code (e.g., a Hadamard code) using analog receive circuitry. Subsequently, data obtained over a sequence of multiple acquisitions may be decoded using digital receive circuitry (e.g., by using an appropriate sequence of additions and subtractions). In the foregoing example, all of the control data for performing coded aperture imaging may be stored in memory of the ultrasound probe prior to receipt of an initiation command that initiates imaging. Such control data may include, for example, data indicative of one or more waveforms, data indicative of one or more inverted versions of the waveforms, and data indicative of the timing with which one or more components of the ultrasound probe, including transmit circuitry, receive circuitry, and/or waveform generator(s), must be activated or deactivated in order to effect coded aperture imaging.

In some embodiments, an ultrasound probe may be configured to perform imaging in a cross-sectional imaging mode. Performing imaging in a cross-sectional imaging mode may comprise performing a sequence of acquisitions in which different acquisitions in the sequence are used to image different cross sections of the subject being imaged. For example, one or more acquisitions in the sequence may be used to image a cross-section of the subject translated vertically from, having a different azimuth angle and/or elevation angle than a cross-section of the subject imaged via one or more other acquisitions in the sequence of acquisitions. An ultrasound probe may be configured to perform cross-sectional imaging in any other suitable way, as aspects of the technology described herein are not limited in this respect. In the foregoing example, all of the control data for performing cross-sectional imaging may be stored in memory of the ultrasound probe prior to receipt of an initiation command that initiates imaging. Such control data may include, for example, data indicative of the parameters and timing with which one or more components of the ultrasound probe, including transmit circuitry, receive circuitry, and/or waveform generator(s), must be activated or deactivated in a sequence in order to effect cross-sectional imaging.

In some embodiments, an ultrasound probe may be configured to perform imaging in an en face imaging mode. Performing imaging in an en face imaging mode may comprise performing a sequence of acquisitions in which different acquisitions in the sequence are used to image different portions of the subject at a same limited depth range. For example, one acquisition in the sequence may be used to image a portion of the subject (e.g., a point, a small region, a cross section) at a depth of approximately three centimeters away from the face of the probe and another acquisition in the sequence may be used to image a different portion of the subject. The data obtained from the sequence of acquisitions may then be used to form an image of an area in the subject that is parallel to the plane of a face of the ultrasound probe. An ultrasound probe may be configured to perform en face imaging in any other suitable way, as aspects of the technology described herein are not limited in this respect. In the foregoing example, all of the control data for performing en face imaging may be stored in memory of the ultrasound probe prior to receipt of an initiation command that initiates imaging. Such control data may include, for example, data indicative of the parameters and timing with which one or more components of the ultrasound probe, including transmit circuitry, receive circuitry, and/or waveform generator(s), must be activated or deactivated in a sequence in order to effect en face imaging.

In some embodiments, an ultrasound probe may be configured to perform imaging in a Doppler imaging mode (e.g., a pulsed wave Doppler imaging mode, a continuous wave Doppler imaging mode, a color Doppler imaging mode, a power Doppler imaging mode, and/or any suitable combination of the above listed Doppler imaging modes). Performing imaging in any of the above-listed Doppler imaging modes may comprise performing a sequence of acquisitions and performing subsequent processing (e.g., Fourier analysis, time-frequency analysis, etc.) to extract Doppler information. Any of the techniques known in the art for extracting Doppler information from a sequence of ultrasound acquisitions may be used. Indeed, an ultrasound probe may be configured to perform Doppler imaging using a sequence of acquisitions in any suitable way, as aspects of the technology described herein are not limited in this respect. In the foregoing example, all of the control data for performing Doppler imaging may be stored in memory of the ultrasound probe prior to receipt of an initiation command that initiates imaging. Such control data may include, for example, data indicative of one or more waveforms (e.g., pulsed wave, continuous wave, etc.) and data indicative of the timing with which one or more components of the ultrasound probe, including transmit circuitry, receive circuitry, and/or waveform generator(s), must be activated or deactivated in order to effect Doppler imaging.

In some embodiments, an ultrasound probe may be configured to perform imaging in a perturbation imaging mode. Performing imaging in a perturbation imaging mode may comprise performing a sequence of acquisitions in which one or more acquisitions are used to perturb the subject being imaged and one or more other acquisitions are used to image the perturbed subject. For example, in some embodiments, performing perturbation imaging may comprise performing one or more acquisitions to induce a shear wave in the subject being imaged and one or more subsequent acquisitions to image the effect of the shear wave on the subject (e.g., to obtain information about the speed of propagation of the shear wave through the subject being imaged). An ultrasound probe may be configured to perform perturbation imaging in any other suitable way, as aspects of the technology described herein are not limited in this respect. In the foregoing example, all of the control data for performing perturbation imaging may be stored in memory of the ultrasound probe prior to receipt of an initiation command that initiates imaging. Such control data may include, for example, data indicative of one or more waveforms used to perturb the subject being imaged and data indicative of the timing with which one or more components of the ultrasound probe, including transmit circuitry, receive circuitry, and/or waveform generator(s), must be activated or deactivated in order to effect perturbation imaging.

In some embodiments, an ultrasound probe may be configured to perform imaging in a compounded imaging mode. Performing imaging in a compounded imaging mode may comprise performing a sequence of acquisitions in which one or more parameters of the emitted ultrasound signals are varied for acquisitions in the sequence and the corresponding sequence of acquired data is subsequently combined (coherently or non-coherently) to form a compound image. For example, performing imaging in a frequency-compounded imaging mode may comprise performing multiple acquisitions at different frequencies (e.g., using different center frequencies such as, for example, 2 MHz and 5 MHz) and coherently (or non-coherently) combining the data acquired during the multiple acquisitions. An ultrasound probe may be configured to perform compounded imaging for any other suitable parameter(s) and/or in any other suitable way, as aspects of the technology described herein are not limited in this respect. In the foregoing example, all of the control data for performing compounded imaging may be stored in memory of the ultrasound probe prior to receipt of an initiation command that initiates imaging. Such control data may include, for example, data indicative of one or more parameters (e.g., center frequencies) to vary in a sequence of acquisitions and data indicative of the timing with which one or more components of the ultrasound probe, including transmit circuitry, receive circuitry, and/or waveform generator(s), must be activated or deactivated in order to effect compounded imaging.

In some embodiments, an ultrasound probe may be configured to perform imaging in a sensor-dependent imaging mode. Performing imaging in a sensor-dependent imaging mode may comprise performing a sequence of acquisitions in which parameters governing one or more of the acquisitions in the sequence are changed, during imaging, based at least in part on information obtained by one or more non-acoustic sensors onboard the probe (e.g., onboard sensors 322 described with reference to FIG. 3). For example, as described in more detail below, a probe may comprise a temperature sensor configured to sense the temperature of the probe's circuitry and upon detecting, via the temperature sensor, that the temperature of the probe's circuitry exceeds a threshold, one or more parameters of the acquisitions in the sequence may be changed (e.g., fewer pulses may be emitted, lower power pulses may be emitted, fewer ultrasonic transducers may be used to emit and/or receive ultrasound signals, etc.). As another example, a probe may comprise one or more motion sensors (e.g., one or more accelerometers) configured to detect movement of the probe and upon detecting, via the motion sensor(s), movement of the probe, one or more parameters for controlling how the acquisitions in the sequence are performed may be changed to adjust the imaging to account for (e.g., counteract the effects of) the probe's motion. In the foregoing example, all of the control data for performing sensor-dependent imaging may be stored in memory of the ultrasound probe prior to receipt of an initiation command that initiates imaging. Such control data may include, for example, data indicative of one or more acquisition parameters (e.g., number of pulses, pulse power, etc.) and/or timing of acquisitions to vary in response to receipt of particular data or signals from one or more sensors.

The above-described ultrasound modes are illustrative and non-limiting examples of imaging modes that an ultrasound probe may be configured to autonomously perform in accordance with some embodiments. Other examples of imaging modes than an ultrasound probe may be configured to autonomously perform include, but are not limited to, A-mode imaging, B-mode imaging, C-mode imaging, M-mode imaging, and pulse inversion imaging.

Figure 3:
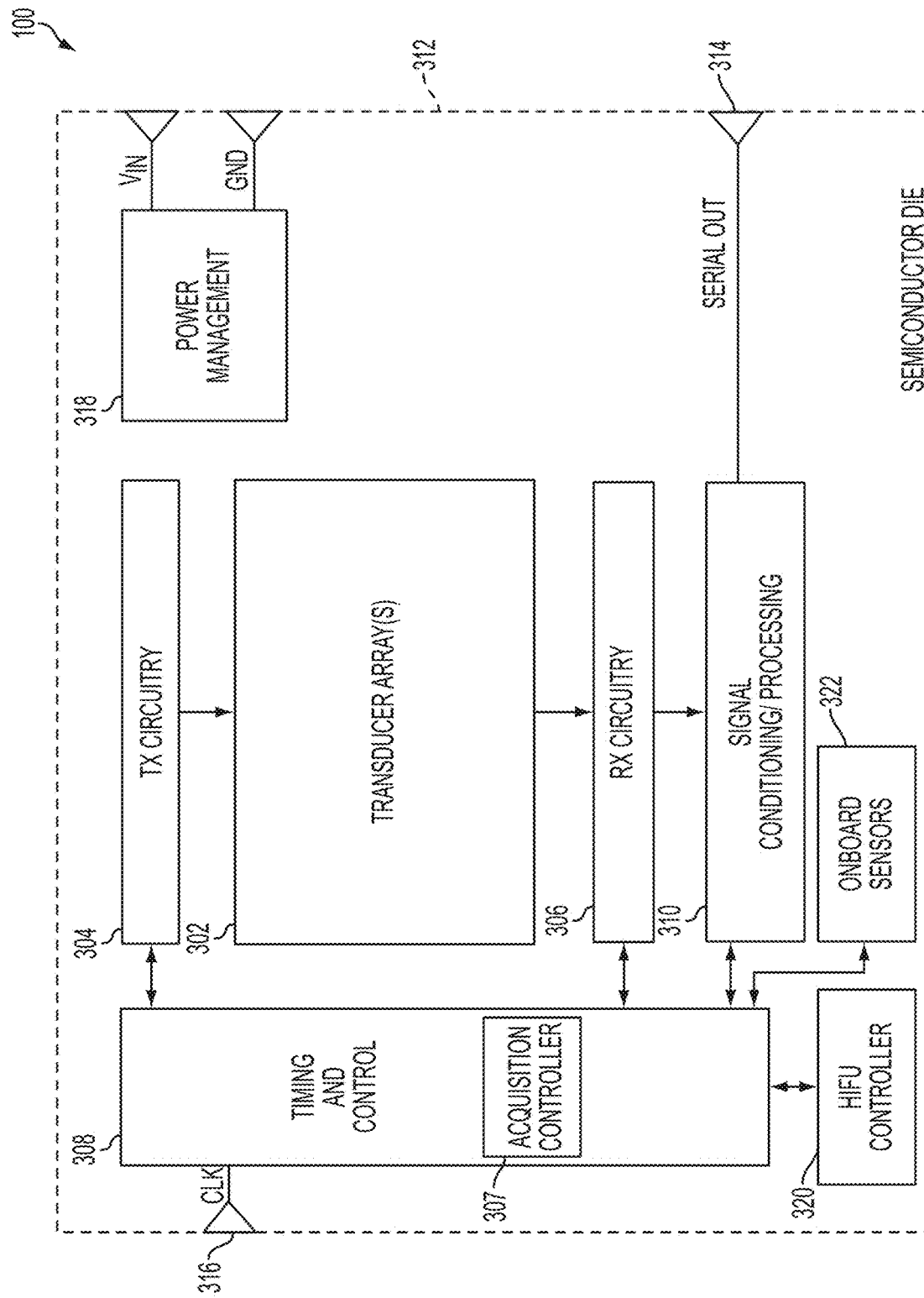
FIG. 3 illustrates an example of an autonomous ultrasound probe which may include an acquisition controller, in accordance with some embodiments of the technology described herein.

FIG. 3 describes illustrative components of autonomous ultrasound probe 100, in accordance with some embodiments of the technology described herein. The ultrasound probe 100 includes one or more transducer arrangements (e.g., arrays) 302 of ultrasonic transducers, transmit (TX) circuitry 304, receive (RX) circuitry 306, timing and control circuitry 308, signal conditioning/processing circuitry 310, and/or a power management circuit 318 receiving ground (GND) and voltage reference (VIN) signals. Some embodiments of transmit circuitry 304 are described in greater detail below with respect to FIG. 5. Some embodiments of receive circuitry 306 are described in greater detail below with respect to FIGS. 6A-6B. Some embodiments of transducer arrangements 302 are described in greater detail below with respect to FIG. 7.

The ultrasound probe 100 may include an acquisition controller 307, which may be implemented as a processor, for controlling other circuitry of the ultrasound probe to perform a sequence of acquisitions governed by control data stored on the ultrasound probe. The acquisition controller 307 may be part of the timing and control circuitry 308, or may be separate in other embodiments. In general, the timing and control circuitry 308 may include suitable circuitry for controlling operation of the transmit circuitry 304, receive circuitry 306, onboard sensors 322, and/or any other suitable components of ultrasound probe 100. Optionally, a high intensity focused ultrasound (HIFU) controller 320 may be included if the ultrasound probe 100 is to be used to provide HIFU.

The ultrasound probe 100 may include one or more onboard sensors 322, which may sense data about the probe and/or its environment. Sensors 322 are "onboard" in the sense that they may be integrated with ultrasound probe 100, which may be done in any suitable way. For example, onboard sensors 322 may be discrete components on ultrasound probe 100, may be integrated with the ultrasound transducers on the same substrate, etc. Sensors 322 may include one or more non-acoustic sensors of any suitable type and, for example, may include one or more accelerometers, gyroscopes, or other sensors indicating movement of the probe, one or more temperature sensors indicating the temperature of the probe (e.g., the temperature of the probe's circuitry), one or more sensors indicating an amount of power used by the probe, one or more pressure sensors, and/or any other suitable type(s) of sensors.

The onboard sensors 322 may obtain data about the probe and/or its environment when the probe is performing imaging, and the probe (e.g., acquisition controller 307) may adapt the way in which it performs the imaging, processes data acquired during imaging, and/or initiates imaging based at least in part on the data acquired by onboard sensors 322. For example, onboard sensors 322 may obtain data indicating that the probe has moved (e.g., a handheld probe may be moved inadvertently due to movement of the user's hand) and the probe may use the obtained data to adjust the way in which it performs imaging to account for the motion (e.g., by using beam steering or other techniques to continue imaging the same portion of the subject as was being imaged prior to the motion or by suitably post-processing the acquired data to account for the motion). As another example, onboard sensors 322 may obtain data indicating that the temperature of at least one component of the probe (e.g., the probe's circuitry) has exceeded a desired threshold and the probe may adjust the way in which it performs imaging to reduce the probe's temperature (e.g., by reducing the power of the transmitted pulses, by reducing the frequency at which the probe emits pulses, by performing less processing of the acquired data, etc.). As yet another example, onboard sensors 322 may obtain data indicating that the power used by the probe has exceeded a desired threshold and the probe may adjust the way in which it performs imaging to reduce the amount of power utilized by the probe (e.g., by reducing the power of the transmitted pulses, by reducing the frequency at which the probe emits pulses, by reducing the number of ultrasonic elements used to transmit and/or receive data, etc.) relative to the amount of power that would have been used by the probe if it continued to perform imaging without adjustment. It should be appreciated that the onboard sensors 322 may also collect data when the probe is not performing imaging and the collected data may be used to control the manner in which imaging is subsequently performed and/or the way data acquired as a result of imaging is processed.

Accordingly, in some embodiments, ultrasound probe 100 may receive an indication to perform an acquisition task (e.g., from host device 104), receive non-acoustic data obtained by one or more of the onboard sensors 322, and control, based on the non-acoustic data and control data for the acquisition task stored on the ultrasound probe 100, the ultrasound probe 100 to obtain acoustic data for the acquisition task. This may be done in any suitable way. For example, in some embodiments, the control data may comprise multiple parameters governing performance of the acquisition task and one or more of the multiple parameters may be selected, based on the non-acoustic data, and used for controlling the ultrasound probe 100 to obtain acoustic data for the acquisition task. In some embodiments, the control data may comprise multiple parameters governing performance of the acquisition task and the value(s) of one or more of the multiple parameters may be adjusted, based on the non-acoustic data, to obtain parameter values to be used in controlling the ultrasound probe 100 to obtain acoustic data for the acquisition task.

Any suitable component(s) of ultrasound probe 100 may be controlled based, at least in part, on the non-acoustic data including, but not limited to, ultrasonic transducer arrangements 302, transmit circuitry 304, and receive circuitry 306.

In the embodiment shown in FIG. 3, all of the illustrated components are formed on a single semiconductor die (or substrate or chip) 312, and thus the illustrated embodiment is an example of an ultrasound on a chip device. However, not all embodiments are limited in this respect. In addition, although the illustrated example shows both TX circuitry 304 and RX circuitry 306, in alternative embodiments only TX circuitry or only RX circuitry may be employed. For example, such embodiments may be employed in a circumstance in which the ultrasound probe is operated as a transmission-only device to transmit acoustic signals or a reception-only device used to receive acoustic signals that have been transmitted through or reflected by a subject being ultrasonically imaged, respectively.

The ultrasound probe 100 further includes a serial output port 314 to output data serially to a host (e.g., serial output port 314 may be used to output data to a host device at act 210 of process 200 described above). The ultrasound probe 100 may also include a clock input port 316 to receive a clock signal (e.g., from a host device such as device 104) and provide the received clock signal CLK to the timing and control circuit 308.

Figure 4:
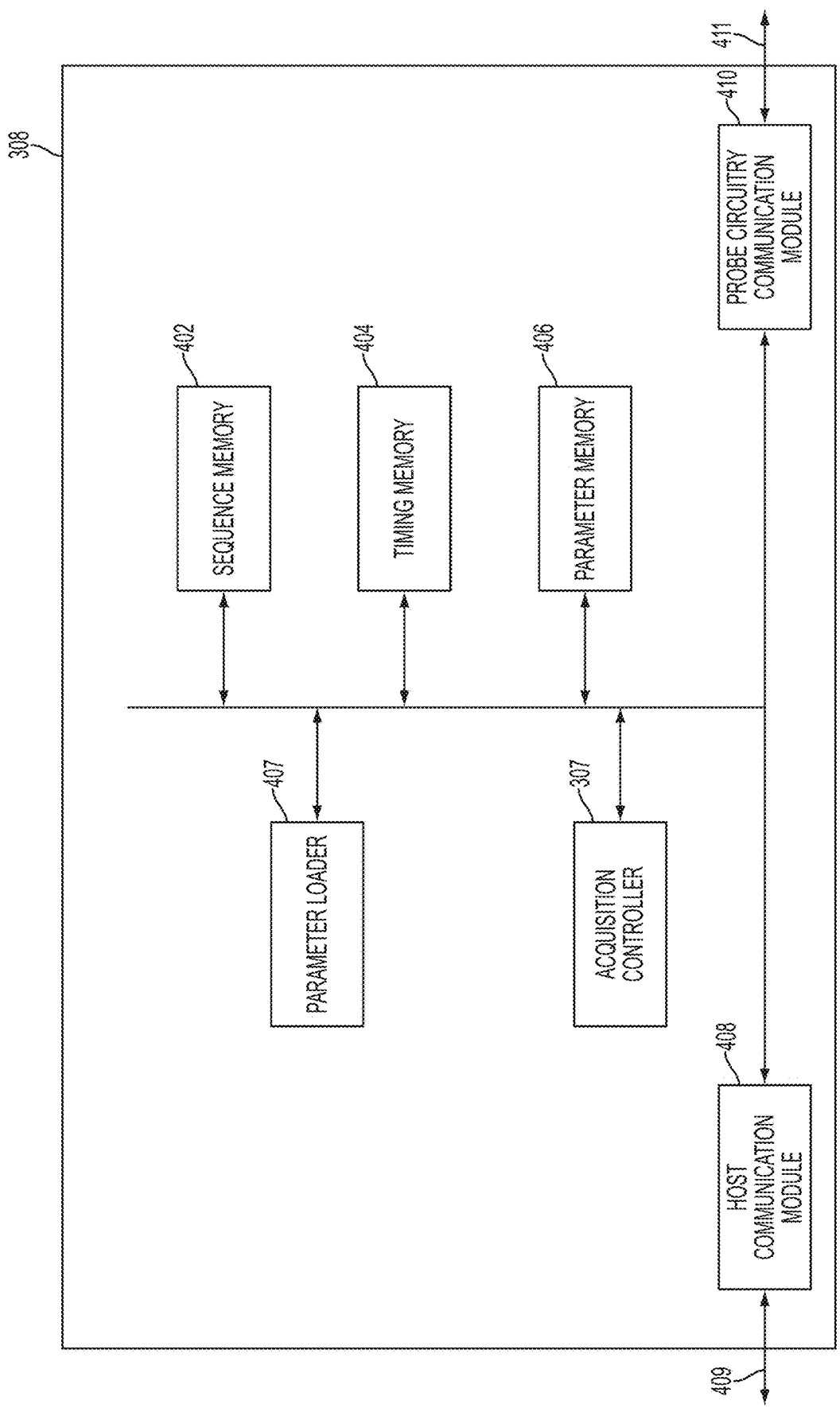
FIG. 4 illustrates an example of timing and control circuitry of an autonomous ultrasound probe including an acquisition controller configured to control circuitry of the ultrasound probe to perform a sequence of acquisitions governed by control data stored on the probe, in accordance with some embodiments of the technology described herein.

FIG. 4 illustrates in block diagram form a non-limiting example of timing and control circuitry 308 of an autonomous ultrasound probe (e.g., ultrasound probe 100). The timing and control circuitry 308 includes an acquisition controller 307, sequence memory 402 for storing information about sequences of acquisitions corresponding to each of one or more imaging modes the ultrasound probe may be configured to perform autonomously, timing memory 404 and parameter memory 406 respectively storing timing and parameter values governing operation of the probe's circuitry in performing various types of acquisitions, parameter loader 407 for loading parameter and timing values into appropriate programmable circuitry of the ultrasound probe, host communication module 408 for communicating (sending and receiving) signals 409 with an external host device (not shown, but an example of which is host device 104), and a probe circuitry communication module 410 for communicating (sending and receiving) signals 411 to the probe's other circuitry (e.g., transmit circuitry, receive circuitry, ultrasound element array, etc.). Data output by one or more ultrasound elements may be received via probe circuitry communication module 410 and may be, in whole or in part, stored in local memory of the ultrasound probe and/or provided to host communication module 408 for communication to the host.

In the embodiment illustrated in FIG. 4, control data governing operation of the ultrasound probe during imaging in one or more imaging modes is stored in sequence memory 402, timing memory 404, and parameter memory 406. Sequence memory 402 stores sequences of acquisitions for respective imaging modes. That is, to perform a desired imaging mode, a sequence of acquisitions stored in sequence memory 402 is performed. For each particular acquisition in a sequence of acquisitions, sequence memory 402 may include information (e.g., pointers) indicating where in timing memory 404 and parameter memory 406 are stored the timing values and parameter values to be used for configuring the probe's circuitry to perform the particular acquisition. Though sequence memory 402, timing memory 404 and parameter memory 406 are illustrated separately in FIG. 4, this is for purposes of illustration only, and all the data stored in these memories may be stored in one or multiple memories on the probe, as aspects of the technology described herein are not limited in this respect.

Each of the memories 402, 404, and 406 may be loaded by the host (e.g., host 104) via the host communication module 408 as part of signals 409. The memories on the probe may be loaded prior to the probe performing imaging (e.g., loaded onto the probe at time of purchase, upon the probe being turned on, etc.). The data stored in the memories 402, 404, and 406 may be raw binary data at least some of which may be loaded into the programmable circuitry of the ultrasound probe as is, in some embodiments, or which may be processed to generate desired configuration data in alternative embodiments. The parameter and timing data stored in the memories 404 and 406 may be indexed, for example with pointers, and therefore need not be stored in a defined order or format in some embodiments.

The timing memory 404 and parameter memory 406 may store timing and parameter data, respectively, relating to a variety of an ultrasound probe's components depending, for example, on the programmable circuitry included in the probe. The types of programmable circuitry depend, in some embodiments, on the desired functionality of the ultrasound probe, and thus the aspects of the present application are not limited to an ultrasound probe having any particular type of programmable circuitry. For example, if it is desired to provide flexibility in terms of the types of waveforms generated by the ultrasound probe, a programmable waveform generator may be provided. The exact type of waveform generator used is not limiting of the various aspects described herein. In some embodiments, programmable delay elements, or a programmable delay mesh (representing a network of multiple delay elements) may be provided to allow flexibility in setting the delay characteristics of the waveforms generated by the ultrasound probe. In some embodiments, variability in the receive functionality of the ultrasound probe may be desired, and thus programmable receive circuitry may be included, such as programmable ADCs, programmable filters and/or programmable modulators, among other possible examples. Non-limiting examples of programmable transmit and receive circuitry are described in connection with FIGS. 5, 6A, and 6B to illustrate the types of circuitry for which timing and parameter data may be stored in memories 404 and 406, respectively.

The host communication module 408 provides for communication of signals 409 between timing and control circuitry 308 and a host, such as host 104 of FIG. 1. As a non-limiting example, the host communication module 408 may be a USB bridge module when the ultrasound probe is coupled to the host via a USB connector, and the signals 409 may be of the type capable of being transferred over a USB connector.

The parameter loader 407 may be a hardware module operating in conjunction with handler state machines which handle the loading of timing and/or parameter values stored in memories 404 and 406 into the ultrasound element communication module 410 to be sent to the ultrasound modules of the ultrasound probe as part of signals 411.

The acquisition controller 307 may be a hardware module (e.g., a processor, circuitry implemented via one or more Field Programmable Gate Arrays, an application-specific integrated circuit, etc.) configured to receive an initiation command from an external device (e.g., via host communication module 408) to begin imaging in a desired imaging mode and start execution of an acquisition sequence corresponding to the imaging mode that is stored in sequence memory 402. For each acquisition in the acquisition sequence, the sequence memory may store pointers to the location of timing and parameter values for controlling performance of the acquisition in memories 404 and 406, respectively, and the acquisition controller 307 may cause parameter loader 407 to provide these timing and parameter values to appropriate programmable circuitry (e.g., to programmable circuitry shown in FIGS. 5, 6A-6B, and 7) of the ultrasound probe to cause the probe to perform the acquisition.

Figure 5:
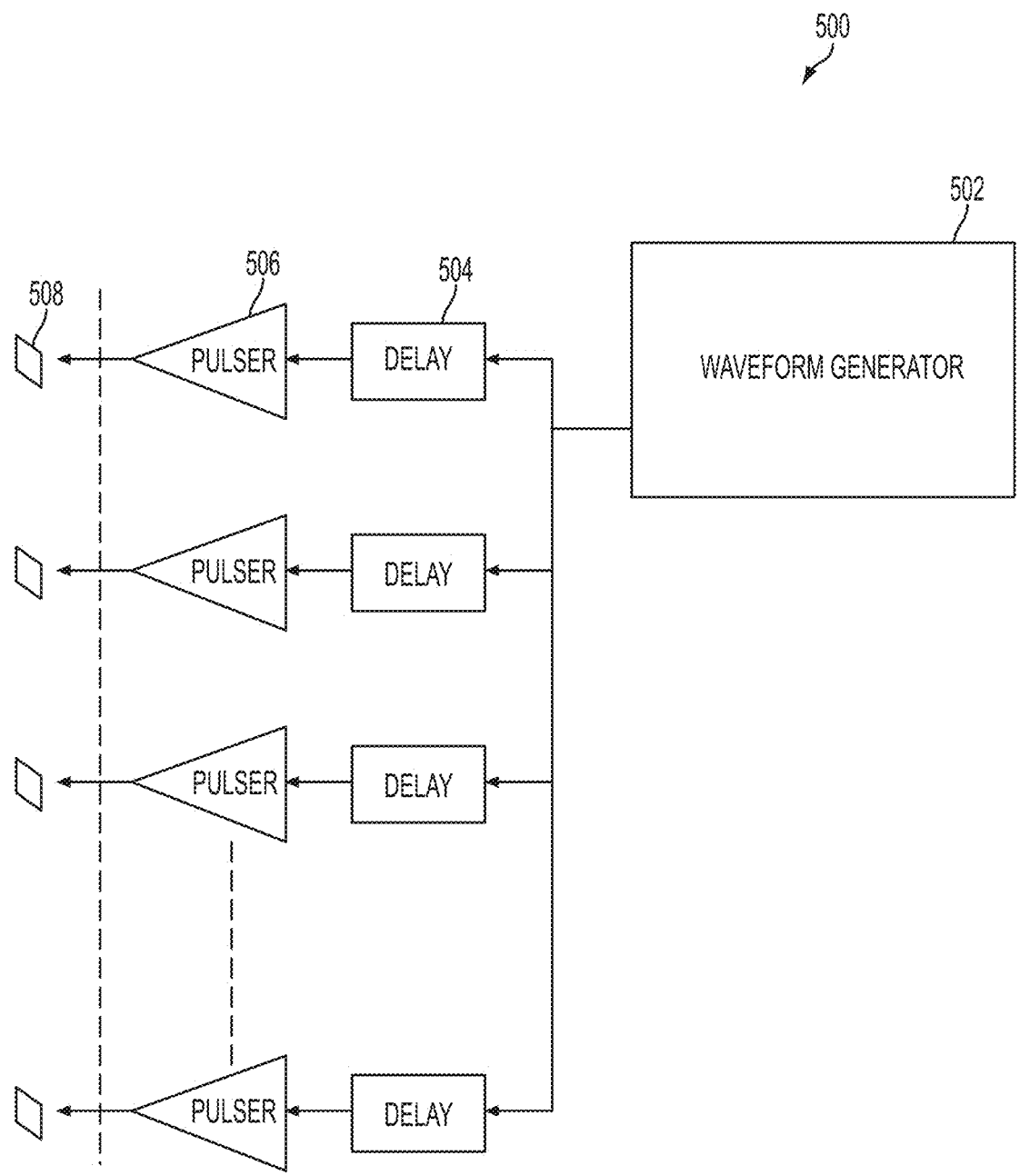
FIG. 5 illustrates an example of a transmit channel of an autonomous ultrasound probe, in accordance with some embodiments of the technology described herein.

FIG. 5 illustrates in block diagram form an example of a transmit channel 500 of an autonomous ultrasound probe (e.g., ultrasound probe 100) including programmable components (e.g., the transmit circuitry 304). The transmit channel 500 includes a waveform generator 502, delay units 504, pulsers 506, and ultrasound elements 508. One or more of these components may be programmable, such that operating the ultrasound probe may involve providing such components with parameter data. For example, the waveform generator 502 and/or delay units 504 may be programmable, as non-limiting examples. As a further specific example, the waveforms generated by the waveform generator 502 may be controlled in that, for example, the frequency, amplitude, phase, and/or rate of change of waveforms generated by the waveform generator 502 may be selected by setting registers of the waveform generator. In this way, the waveform generator 502 may be configured to (e.g., programmable to) generate various types of waveforms including, but not limited to, impulses, continuous waves, chirp waveforms (e.g., linear frequency modulation (LFM)) chirps, and coded excitations (e.g., binary coded excitations).

Similarly, the delay units 504 may be programmable. In the illustrated embodiment of FIG. 5, each delay unit 504 receives a waveform from the waveform generator 502, but in other embodiments the delay units 504 may be coupled together, for example to form a programmable delay mesh in which waveforms may be passed from one delay unit to another. Operating features of a particular delay unit such as the amount of time/samples by which to delay a waveform input to the delay unit (e.g., from a waveform generator, from another delay unit when the delay unit is part of a programmable mesh, etc.), which direction to pass the waveform (e.g., to a neighboring delay unit on the right or a neighboring delay unit on the left, forward, etc.), and whether to provide the waveform to a pulser may be programmed by setting parameter values of the delay unit. In this way, the programmable delay mesh may be programmed via setting parameters of its constituent delay units.

Figure 6A:
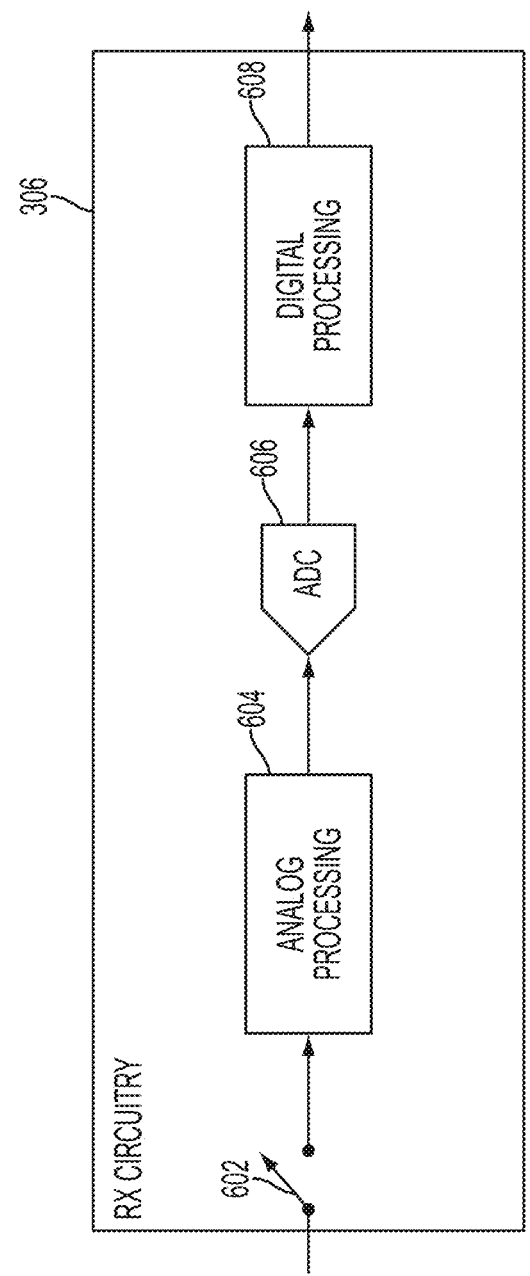
FIGS. 6A and 6B illustrate an example of a receive channel of an autonomous ultrasound probe, in accordance with some embodiments of the technology described herein.
Figure 6B:
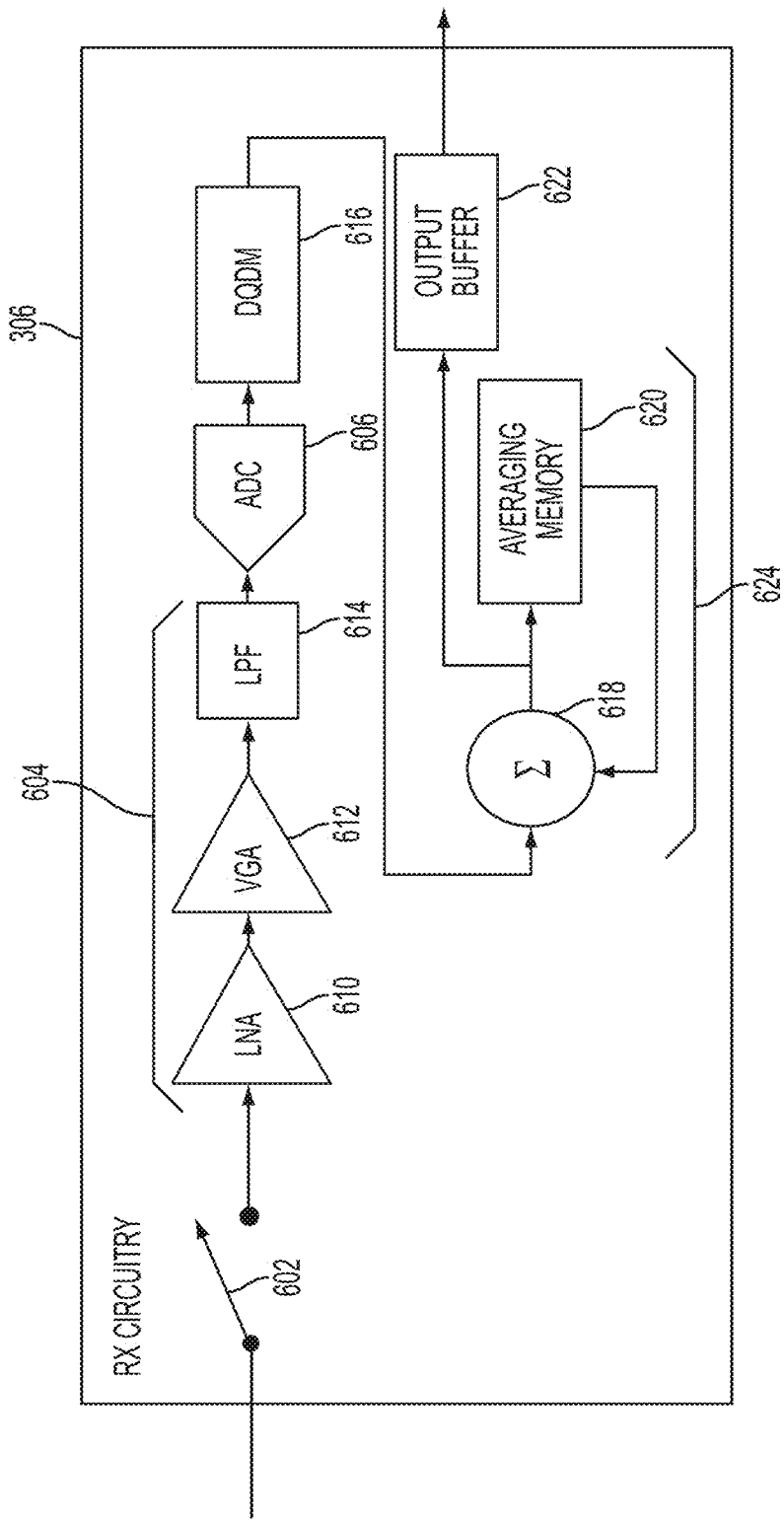

FIGS. 6A and 6B illustrate an example of the circuitry, both analog and digital, which may be included as part of a receive channel of an ultrasound probe (e.g., the receive circuitry 306 of autonomous ultrasound probe 100). For example, the receive circuitry 306 and/or signal conditioning/processing circuitry 310 of FIG. 3 may include one or more of the components illustrated in FIGS. 6A and 6B. It should be appreciated that the components of FIGS. 6A and 6B represent non-limiting examples, and that alternative components and arrangements may be implemented consistent with aspects of the present application. The receive circuitry illustrated in FIGS. 6A and 6B may be dedicated receive circuitry for a respective ultrasound transducer element of an ultrasound probe, may be receive circuitry configurable or configured to process data acquired by any one or more of multiple ultrasound transducer elements.

As shown in FIG. 6A, the receive circuitry for a transducer element includes analog processing receive circuitry 604, an analog-to-digital converter (ADC) 606, and digital processing receive circuitry 608. The ADC 606 may be, for example, a 10-bit, a 12-bit, a 20 mega-sample per second (Msps), a 40 Msps, a 50 Msps, or a 80 Msps ADC. A receive control switch 602 may be provided and may be closed when the ultrasound probe is operating in a receive mode.

FIG. 6B shows illustrative components of analog processing receive circuitry 604 including, for example, a low-noise amplifier (LNA) 610, a variable-gain amplifier (VGA) 612, and a low-pass filter (LPF) 614. In some embodiments, the VGA 612 may be adjusted, for example, via a time-gain compensation (TGC) circuit. The LPF 614 provides for anti-aliasing of the acquired signal. In some embodiments, the LPF 614 may comprise, for example, a second-order low-pass filter having a frequency cutoff at approximately 5 MHz. However, other implementations are possible and contemplated.

FIG. 6B also shows illustrative components of digital processing receive circuitry 608 including, for example, a digital quadrature demodulation (DQDM) circuit 616, an accumulator 618, an averaging memory 620, and an output buffer 622. The accumulator 618 and averaging memory 620 together may form an averaging circuit 624.

The DQDM circuit 616 may be configured, for example, to demodulate down the digitized version of the received signal from center frequency to baseband, and then low-pass filter and decimate the demodulated signal. The DQDM 616 may include, for example, a mixer block, a low-pass filter (LPF), and a decimator circuit. The illustrated circuit of FIG. 6B may allow for a reduction (lossy or lossless) of bandwidth by removing frequencies from the received signal, thus significantly reducing the amount of digital data that needs to be processed by the signal conditioning/processing circuit 310 and offloaded from the die 312.

While programmable circuitry components have been described in connection with FIGS. 5, 6A, and 6B with respect to the transmit and receive functionality of an autonomous ultrasound probe, it should be appreciated that ultrasound probes to which aspects of the present application may apply may additionally include programmable circuitry which is not specific to transmit or receive functions of the ultrasound probe. As one example, timing circuitry and general control circuitry (e.g., timing and control circuit 308) may include one or more programmable features. Thus, control data stored on an autonomous ultrasound probe may include parameter and timing data related to these other types of circuitry as well for each of one or more types of acquisitions that the probe may be configured to perform autonomously.

It should be appreciated from the foregoing discussion that ultrasound probes may include various circuitry (analog and/or digital) and therefore that in order to perform a sequence of acquisitions autonomously, an ultrasound probe may need to store various control data (including parameter values and timing values) used to configure (e.g., program circuitry of) a given ultrasound probe depending on which circuitry components are included in that probe and what mode of operation is being performed. For clarity, a brief summary of non-limiting examples of parameter values for which parameter data may be stored and loaded on an ultrasound probe is now provided.

In some embodiments, an ultrasound probe may include a programmable waveform generator (e.g., waveform generator 502). Programming the waveform generator may involve specifying one or more of the following: waveform delay; waveform amplitude; waveform duration (total length of waveform); waveform envelope; initial phase of the waveform; initial frequency of the waveform; chirp rate (if a chirp is to be generated); invert bit (to invert the waveform); and coded-excitation (a bit enabling shifting of the chirp rate parameter for use with a coded-excitation).

In some embodiments, a programmable delay unit or delay mesh may be provided as part of an ultrasound probe. The types of programmable features will depend on the specific type of programmable delay element used. For purposes of illustration, it can be assumed that the delay unit is coupled to a pulser and includes a buffer or other memory with multiple storage locations. In this case, examples of programmable features of a delay unit may include: write select, to select to which location of the delay unit memory to write data; read select to select from which location of the delay unit memory to read data; pulser enable (to enable a pulser to which the delay unit may be coupled); delay unit enable (to enable or disable the delay unit itself); and an invert bit (to invert the signal (e.g., waveform) being delayed by the delay unit).

Components which operate as part of the receive functionality of an ultrasound probe may also be programmable. For example, as described previously, an ultrasound probe may include a DQDM module, a LPF, a data averaging block, and a sample memory. Parameters associated with one or more such components may be set. For example, with respect to the data averaging block, parameters such as bit shift, word extend, and accumulate may be set. Variable bit-width memory packing of the memory may also be set.

As described previously, an autonomous ultrasound probe according to an aspect of the present application includes circuitry arranged in a modular configuration. An example is illustrated in FIG. 7, representing a non-limiting implementation of the ultrasound probe 100 of FIG. 1.

Figure 7:
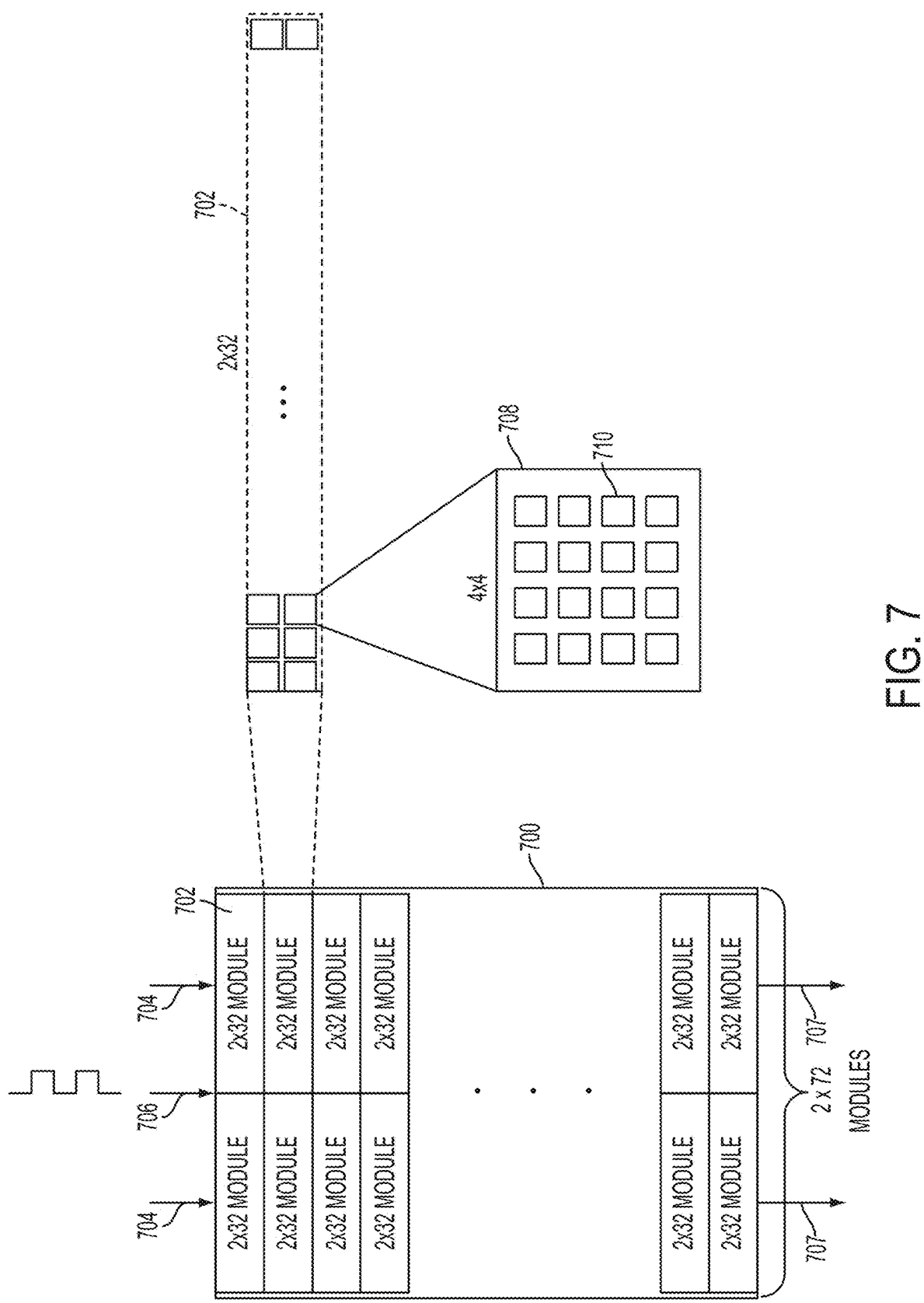
FIG. 7 illustrates an example of an ultrasound probe having a plurality of like ultrasound modules coupled together and including programmable circuitry, in accordance with some embodiments of the technology described herein.

As shown in FIG. 7, the ultrasound probe 700 includes a plurality of ultrasound modules 702 arranged in two rows (or columns, depending on orientation). In this non-limiting example, there are 72 such ultrasound modules per row, giving a total of 144 such ultrasound modules 702 for the ultrasound probe 700. In this example, the ultrasound modules are identical to one another, each including respective transmit circuitry, ultrasound transducers, and receive circuitry. In the illustrated non-limiting example, the ultrasound modules 702 each include two columns of 32 ultrasound elements 708 for a total of 64 ultrasound elements 708 per ultrasound module 702 as shown in the inset of FIG. 7, and accordingly are referred to herein as 2×32 modules. However, it should be appreciated that the aspects of the present application are not limited to ultrasound modules having any particular number of ultrasound elements, and that a 2×32 module is an example described for purposes of illustration.

The ultrasound modules 702 of each row are coupled such that data (e.g., parameter data) may be transferred from one ultrasound module 702 to a neighboring ultrasound module 702. The coupling may be a daisy-chain configuration (a ring network), although alternatives are possible, such as alternative array configurations. Data 704, such as control data including parameter values and timing values, is provided to the first ultrasound module of each row of the ultrasound modules 702 and a global clock signal 706 is provided to all the ultrasound modules 702. The global clock signal may be any suitable clock frequency, a non-limiting example of which is 200 MHz. Data out 707 is provided by the ultrasound modules 702, and may represent collected raw data or processed imaging data in some embodiments.

In addition to one or more ultrasonic transducers, an ultrasound module 702 may comprise various types of circuitry including, but not limited to, one or more waveform generators (e.g., two waveform generators, four waveform generators, etc.), encoding circuitry, delay mesh circuitry, and/or decoding circuitry. These examples of circuitry that may be part of an ultrasound module 702 are illustrative and are not limiting, as an ultrasound module may additionally or alternatively comprise any other suitable circuitry.

Ultrasound element 708 may include one or more ultrasonic transducers 710 (also referred to herein as "transducer cells"). Stated differently, ultrasonic transducers 710 may be grouped together to form ultrasound elements 708. In the illustrated embodiment of FIG. 7, each ultrasound element 708 comprises 16 ultrasonic transducers 710 arranged as a two-dimensional array having four rows and four columns. However, it should be appreciated that an ultrasound element 708 may comprise any suitable number of ultrasonic transducers (e.g., one, at least two, at least four, at least 16, at least 25, at least 36, at least 49, at least 64, at least 81, at least 100, between one and 200, more than 200, thousands, etc.).

The ultrasonic transducers 710 may be any suitable type of ultrasonic transducers, including capacitive micromachined ultrasonic transducers (CMUTs) or piezoelectric transducers. CMUTs may be used if the ultrasound probe is to include integrated circuitry and ultrasonic transducers.

While the ultrasound probe 700 includes 144 modules, it should be appreciated that any suitable number of ultrasound modules may be included (e.g., at least two modules, at least ten modules, at least 100 modules, at least 1000 modules, at least 5000 modules, at least 10,000 modules, at least 25,000 modules, at least 50,000 modules, at least 100,000 modules, at least 250,000 modules, at least 500,000 modules, between two and a million modules, etc.). Some of the benefits provided by aspects of the present application are more readily realized as the number of ultrasound modules increases.

According to some aspects, an ultrasound probe may comprise a single set of timing and control circuitry which may be used to control operation of all ultrasound transducer modules of an ultrasound probe. For example, timing and control circuitry 308, described with reference to FIG. 3, may provide control data, including parameter values and timing values, to configure (e.g., program) ultrasound transducer modules 702. In other embodiments, however, an autonomous ultrasound probe may comprise multiple sets of timing and control circuitry, each of which may be used to configure respective sets of ultrasound modules.

Aspects described herein provide for autonomous ultrasound probes that can autonomously perform imaging in any of numerous imaging modes (each such mode potentially comprising multiple acquisitions). Benefits provided by some aspects of the ultrasound probes described herein include decreased complexity of host devices and the connections between the host devices and the ultrasound probes due to increased autonomy of the probes. Other benefits include increased modularity as the probes may be coupled to numerous types of hosts (e.g., PDAs, smartphones, tablets, laptops, etc.) and more efficient operation as a result of the probes' reduced dependence on control information from the host during imaging.

Provided below are examples of aspects of the technology described herein.

Example 1

An apparatus, comprising: an ultrasound probe configured to store a control data and, in response to receiving an initiation command from a device external to the ultrasound probe, autonomously perform a sequence of ultrasound acquisitions governed by the control data.

Example 2

The apparatus of Example 1, wherein the ultrasound probe is configured to autonomously perform a sequence of ultrasound acquisitions governed by the control data only in response to receiving only an initiation command from the device external to the ultrasound probe.

Example 3

An apparatus, comprising: an ultrasound probe, comprising: memory circuitry configured to store control data governing at least a first type of acquisition, the control data including a first parameter data and a first timing data for the first type of acquisition; transmit circuitry; one or more ultrasound elements; receive circuitry; and at least one controller configured to: receive an indication, from an external device external to the ultrasound probe, to perform an acquisition task; and control, based at least in part on the first parameter data and the first timing data, the transmit circuitry, the one or more ultrasound elements, and the receive circuitry to autonomously perform the acquisition task, in response to receiving the indication, the acquisition task comprising a sequence of acquisitions including at least one acquisition of the first type.

Example 4

The apparatus of Example 3, wherein the first timing data comprises at least one transmit timing value indicating when at least one component of the transmit circuitry is to operate during the at least one acquisition of the first type, and wherein the at least one controller is configured to control the transmit circuitry at least in part by controlling the at least one component of the transmit circuitry to operate in accordance with the at least one transmit timing value.

Example 5

The apparatus of Example 4 or any other preceding Example, wherein the first parameter data comprises at least one transmit parameter value for operating the at least one component of the transmit circuitry during the at least one acquisition of the first type, and wherein the at least one controller is configured to control the transmit circuitry at least in part by controlling the at least one component of the transmit circuitry to operate in accordance with the at least one transmit parameter value.

Example 6

The apparatus of Example 5 or any other preceding Example, wherein the at least one component of the transmit circuitry comprises a pulser; wherein the at least one transmit parameter value comprises at least one pulser parameter value for operating the pulser and the at least one transmit timing value comprises at least one pulser timing value; and wherein the at least one controller is configured to control the transmit circuitry at least in part by controlling the pulser to operate during the sequence of acquisitions in accordance with the at least one pulser parameter value and the at least one pulser timing value.

Example 7

The apparatus of Example 5 or any other preceding Example, wherein the at least one component of the transmit circuitry comprises a waveform generator; wherein the at least one transmit parameter value comprises at least one waveform generator parameter value for operating the waveform generator and the at least one transmit timing value comprises at least one waveform generator timing value; and wherein the at least one controller is configured to control the transmit circuitry at least in part by controlling the waveform generator to operate during the sequence of acquisitions in accordance with the at least one waveform generator parameter value and the at least one waveform generator timing value.

Example 8

The apparatus of Example 5 or any other preceding Example, wherein the at least one component of the transmit circuitry comprises a delay unit; wherein the at least one transmit parameter value comprises at least one delay unit parameter value for operating the delay unit and the at least one transmit timing value comprises at least one delay unit timing value; and wherein the at least one controller is configured to control the transmit circuitry at least in part by controlling the delay unit to operate during the sequence of acquisitions in accordance with the at least one delay unit parameter value and the at least one delay unit timing value.

Example 9

The apparatus of Example 3 or any other preceding Example, wherein the first timing data comprises at least one receive timing value indicating when at least one component of the receive circuitry is to operate during the at least one acquisition of the first type, and wherein the at least one controller is configured to control the receive circuitry at least in part by controlling the at least one component of the receive circuitry to operate in accordance with the at least one receive timing value.

Example 10

The apparatus of Example 9 or any other preceding Example, wherein the first parameter data comprises at least one receive parameter value for operating the at least one component of the receive circuitry during the at least one acquisition of the first type, and wherein the at least one controller is configured to control the receive circuitry at least in part by controlling the at least one component of the receive circuitry to operate in accordance with the at least one receive parameter value.

Example 11

The apparatus of Example 10 or any other preceding Example, wherein the at least one component of the receive circuitry comprises analog receive circuitry; wherein the at least one receive parameter value comprises at least one analog receive circuitry parameter value for operating the analog receive circuitry and the at least one receiving timing value comprises at least one analog receive circuitry timing value; and wherein the at least one controller is configured to control the receive circuitry at least in part by controlling the analog receive circuitry to operate during the sequence of acquisitions in accordance with the at least one analog receive circuitry parameter value and the at least one analog receive circuitry timing value.

Example 12

The apparatus of Example 10 or any other preceding Example, wherein the at least one component of the receive circuitry comprises digital receive circuitry; wherein the at least one receive parameter value comprises at least one digital receive circuitry parameter value for operating the digital receive circuitry and the at least one receive timing value comprises at least one digital receive circuitry timing value; and wherein the at least one controller is configured to control the receive circuitry at least in part by controlling the digital receive circuitry to operate during the sequence of acquisitions in accordance with the at least one digital receive circuitry parameter value and the at least one digital receive circuitry timing value.

Example 13

The apparatus of Example 10 or any other preceding Example, wherein the at least one component of the receive circuitry comprises an analog to digital converter (ADC); wherein the at least one receive parameter value comprises at least one ADC parameter value for operating the ADC and the at least one receive timing value comprises at least one ADC timing value; and wherein the at least one controller is configured to control the receive circuitry at least in part by controlling the ADC to operate during the sequence of acquisitions in accordance with the at least one ADC parameter value and the at least one ADC timing value.

Example 14

The apparatus of Example 3 or any other preceding Example, wherein the ultrasound probe further comprises control circuitry, and wherein the first timing data comprises at least one control circuitry timing value indicating when at least one component of the control circuitry is to operate during the at least one acquisition of the first type, and wherein the at least one controller is configured to control the control circuitry at least in part by controlling the at least one component of the control circuitry to operate in accordance with the at least one control timing value.

Example 15

The apparatus of Example 14 or any other preceding Example, wherein the first parameter data comprises at least one control parameter value for operating the at least one component of the control circuitry during the at least one acquisition of the first type, and wherein the at least one controller is configured to control the control circuitry at least in part by controlling the at least one component of the control circuitry to operate in accordance with the at least one control parameter value.

Example 16

The apparatus of Example 3 or any other preceding Example, wherein the ultrasound probe further comprises control circuitry, and wherein the control circuitry comprises the at least one controller.

Example 17

The apparatus of Example B3 or any other preceding Example, wherein the control data includes second parameter data and second timing data for a second type of acquisition, wherein the sequence of acquisitions includes at least one acquisition of the second type, and wherein the at least one controller is configured to: control, based on the second parameter data and the second timing data, the transmit circuitry, the one or more elements, and the receive circuitry to perform the sequence of acquisitions, in response to receiving the indication.

Example 18

The apparatus of Example 3 or any other preceding Example, wherein the sequence of acquisitions includes a plurality of acquisitions of the first type.

Example 19

The apparatus of Example 19 or any other preceding Example, wherein the sequence of acquisitions includes a plurality of acquisitions of the first type and a plurality of acquisitions of a second type different from the first type.

Example 20

The apparatus of Example 3 or any other preceding Example, wherein the indication to perform a sequence of acquisitions comprises an indication to perform imaging in an imaging mode.

Example 21

The apparatus of claim Example 20 or any other preceding Example, wherein the indication to perform imaging in an imaging mode is an indication to perform imaging in a single illumination acquisition mode.

Example 22

The apparatus of Example 20 or any other preceding Example, wherein the indication to perform imaging in an imaging mode is an indication to perform imaging in a Doppler mode.

Example 23

The apparatus of Example 3 or any other preceding Example, wherein the indication to perform the sequence of acquisitions including at least one acquisition of the first type does not include parameters for performing the at least one acquisition of the first type.

Example 24

The apparatus of Example 3 or any other preceding Example, wherein in response to receiving the indication, the at least one controller is configured to control components of the ultrasound probe to complete performance of the sequence of acquisitions before receiving any other information from the external device.

Example 25

The apparatus of Example 3 or any other preceding Example, wherein the indication is a digital code, a pulse, and/or a trigger signal.

Example 26

An apparatus, comprising: an ultrasound probe storing a parameter data and a timing data for at least a first type of acquisition, the ultrasound probe comprising: circuitry configured to: receive an indication, from an external device external to the ultrasound probe, to perform an acquisition task comprising a sequence of acquisitions including at least one acquisition of the first type; and control, independently from the external device and based at least in part on the parameter data and the timing data, the ultrasound probe to autonomously perform the acquisition task.

Example 27

The apparatus of Example 26, wherein the circuitry controls the ultrasound probe to autonomously perform the sequence of acquisitions by controlling operation of components of the ultrasound probe based, at least in part on, the parameter data and the timing data stored on the ultrasound probe prior to receipt of the indication.

Example 28

The apparatus of Example 27 or any other preceding Example, wherein the indication does not include the parameter data.

Example 29

The apparatus of Example 28 or any other preceding Example, wherein the indication does not include the acquisition timing data.

Having thus described several aspects and embodiments of the technology set forth in the disclosure, it is to be appreciated that various alterations, modifications, and improvements will readily occur to those skilled in the art. Such alterations, modifications, and improvements are intended to be within the spirit and scope of the technology described herein. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

Also, as described, some aspects may be embodied as one or more methods, examples of which have been provided (e.g., the methods described with reference to FIGS. 2A and 2B). The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. An ultrasound probe, including:
   a plurality of ultrasonic transducers;
   a programmable delay mesh coupled to the plurality of ultrasonic transducers, the programmable delay mesh further comprising a plurality of programmable delay units including a first delay unit and a second delay unit coupled to the first delay unit, wherein the first delay unit is capable of passing waveforms to the second delay unit;
   a programmable waveform generator having an output coupled to an input of the programmable delay mesh;
   a motion sensor configured to detect motion of the ultrasound probe; and
   a controller configured to:
      receive an indication, from an external device, to perform an acquisition task;
      configure the ultrasound probe to perform the acquisition task, in response to receiving the indication;
      receive motion data from the motion sensor; and
      while the ultrasound probe is performing the acquisition task, compensate for the motion of the ultrasound probe based on the motion data, wherein the controller is further configured to compensate for the motion of the ultrasound probe, at least in part by adjusting how the ultrasound probe performs the acquisition task by continuing imaging, using beam steering, a same portion of a subject as was being imaged prior to the motion of the ultrasound probe.

2. The ultrasound probe of claim 1, wherein the motion sensor comprises an accelerometer or a gyroscope.

3. The ultrasound probe of claim 1, wherein the controller is further configured to receive the indication from the external device via a digital communication link.

4. The ultrasound probe of claim 1, wherein the controller is further configured to transmit acoustic data to the external device external to the ultrasound probe.

5. A system, comprising:
   the ultrasound probe of claim 1; and
   the external device external to the ultrasound probe, wherein the external device is configured to receive acoustic data from the ultrasound probe and generate an ultrasound image based at least in part on the acoustic data.

6. The ultrasound probe of claim 1, wherein the plurality of ultrasonic transducers further comprises a plurality of capacitive micromachined ultrasonic transducers.

7. The ultrasound probe of claim 1, wherein the plurality of ultrasonic transducers and the motion sensor are integrated on a same substrate.

8. The ultrasound probe of claim 1, wherein the controller is further configured to control the motion sensor to obtain the motion data.

9. The ultrasound probe of claim 1, wherein the controller is configured to compensate for the motion of the ultrasound probe by adjusting how the ultrasound probe performs processing of acoustic data obtained by the ultrasound probe during performance of the acquisition task to counteract the effect of the motion of the ultrasound probe.

10. The ultrasound probe of claim 1, further comprising:
    a plurality of pulsers,
    wherein the plurality of programmable delay units is coupled to the plurality of pulsers, and wherein the plurality of pulsers is coupled to the plurality of ultrasonic transducers.

11. The ultrasound probe of claim 1, wherein the controller is configured to program the programmable waveform generator so that the programmable waveform generator is configured to generate linear frequency modulation chirps.

12. The ultrasound probe of claim 1, wherein the controller is configured to program the programmable waveform generator so that the programmable waveform generator is configured to generate coded excitations.

13. The ultrasound probe of claim 1, wherein the controller is configured to program the programmable waveform generator so that the programmable waveform generator is configured to generate impulses.

14. The ultrasound probe of claim 1, wherein the controller is configured to program the programmable waveform generator so that the programmable waveform generator is configured to generate continuous waves.

15. The ultrasound probe of claim 1, further comprising:
    a memory circuitry storing control data for operating the ultrasound probe to perform the acquisition task.

16. The ultrasound probe of claim 15, wherein the control data comprises a parameter value for controlling the plurality of ultrasonic transducers to obtain acoustic data, and wherein the controller is configured to select the parameter value based on the motion data.

17. The ultrasound probe of claim 15, further comprising a transmit circuitry, wherein the controller is further configured to control, based on the control data and the motion data, the plurality of ultrasonic transducers and the transmit circuitry to obtain acoustic data, wherein the transmit circuitry comprises the programmable waveform generator and the programmable delay mesh.

18. The ultrasound probe of claim 15, wherein the control data comprises a set of predefined parameters, and wherein the controller is further configured to control the plurality of ultrasonic transducers to obtain acoustic data at least in part by controlling the plurality of ultrasonic transducers to obtain one or more discrete acoustic data sets as a function of the motion data and the predefined parameters.

19. The ultrasound probe of claim 15, wherein the control data comprises parameters for the programmable delay mesh and for the programmable waveform generator, and the controller is configured to control, based on the control data, the ultrasound probe to begin autonomously performing the acquisition task, by programming the programmable delay mesh and the programmable waveform generator with the parameters.

20. The ultrasound probe of claim 1, wherein the controller is configured to program the programmable delay mesh to set an amount and/or samples by which to delay a waveform input to the first delay unit.

21. The ultrasound probe of claim 1, wherein the controller is configured to program the programmable delay mesh to set a direction in which the first delay unit is to provide an output waveform.

22. The ultrasound probe of claim 1, wherein the plurality of ultrasonic transducers, the programmable delay mesh, the programmable waveform generator, the motion sensor, and the controller are housed together in the ultrasound probe.

23. An ultrasound apparatus, comprising:
an ultrasound probe physically including a plurality of ultrasonic transducers, a programmable delay mesh coupled to the plurality of ultrasonic transducers, the programmable delay mesh comprising a plurality of programmable delay units including a first delay unit, and a second delay unit neighboring the first delay unit, and a third delay unit neighboring the first delay unit, a programmable waveform generator having an ouput coupled to an input of the programmable delay mesh, a motion sensor to detect motion of the ultrasound probe, a computer-readable storage device, and memory circuitry configured to store control data for operating the ultrasound proble to perform an acquisition task,
wherein the computer-readable storage device comprises instructions that, when executed by the ultrasound probe, cause the ultrasound probe to perform a process comprising:
receiving an indication, from an external device external to the ultrasound probe, to perform the acquisition task;
controlling, based on the control data, the ultrasound probe to begin autonomously performing the acquisition task, in response to receiving the indication, the control data comprising parameters for the programmable delay mesh and for the programmable waveform generator, the controlling comprising programming the programmable delay mesh with at least one of the parameters to specify whether the first delay unit is to provide an output waveform to the second delay unit or to the third delay unit;
receiving, from the motion sensor, motion data obtained by the motion sensor while the ultrasound probe is performing the acquisition task, compensating for the motion of the ultrasound probe,
wherein the controller is further configured to compensate for the motion of the ultrasound probe, at least in part by adjusting how the ultrasound probe performs the acquisition task by continuing imaging, using beam steering, a same portion of a subject as was being imaged prior to the motion of the ultrasound probe.

24. The ultrasound apparatus of claim 23, wherein the control data comprises a parameter value for controlling the plurality of ultrasonic transducers to obtain acoustic data, and wherein the controller is configured to select the parameter value based on the motion data.

25. The ultrasound apparatus of claim 23, wherein the process performed by ultrasound probe further comprises receiving the indication from the external device via a digital communication link.

26. The ultrasound apparatus of claim 23, wherein the controlling further comprises transmitting acoustic data to the external device external to the ultrasound probe.

27. The ultrasound apparatus of claim 23, wherein the ultrasound probe further comprises a transmit circuitry, and wherein the controlling further comprises controlling, based on the control data and the motion data, the plurality of ultrasonic transducers and the transmit circuitry to obtain acoustic data.

28. The ultrasound apparatus of claim 23, wherein the controlling further comprises controlling the motion sensor to obtain the motion data.

29. The ultrasound apparatus of claim 23, wherein the control data comprises a set of predefined parameters, and wherein the controlling further comprises controlling the plurality of ultrasonic transducers to obtain one or more discrete acoustic data sets as a function of the motion data and the predefined parameters.

30. The computer-readable storage device of claim 23, wherein compensating for the motion of the ultrasound probe comprises adjusting how the ultrasound probe performs processing of acoustic data obtained by the ultrasound probe during performance of the acquisition task to counteract the effect of the motion of the ultrasound probe.

* * * * *

UNITED STATES PATENT AND TRADEMARK OFFICE
CERTIFICATE OF CORRECTION

PATENT NO. : 10,695,034 B2
APPLICATION NO. : 14/714150
DATED : June 30, 2020
INVENTOR(S) : Tyler S. Ralston et al.

It is certified that error appears in the above-identified patent and that said Letters Patent is hereby corrected as shown below:

In the Claims

Claim 23, Column 33, Line 34:
"a programmable waveform generator having an ouput"
Should be replaced with:
--a programmable waveform generator having an output--

Claim 23, Column 33, Line 36:
"a motion sensor to detect motion of the ultrasound"
Should be replaced with:
--a motion sensor configured to detect motion of the ultrasound--

Claim 23, Column 33, Line 39:
"operating the ultrasound proble to perform an acquisi-"
Should be replaced with:
--operating the ultrasound probe to perform an acquisi- --

Claim 23, Column 34, Lines 7-17:
"receiving, from the motion sensor, motion data obtained by the motion sensor while the ultrasound probe is performing the acquisition task, compensating for the motion of the ultrasound probe,
wherein the controller is further configured to compensate for the motion of the ultrasound probe, at least in part by adjusting how the ultrasound probe performs the acquisition task by continuing imaging, using beam steering, a same portion of a subject as was being imaged prior to the motion of the ultrasound probe."
Should be replaced with:
--receiving, from the motion sensor, motion data obtained by the motion sensor while the ultrasound probe is performing the acquisition task; and
after receiving the motion data obtained by the motion sensor while the ultrasound probe is performing the acquisition task, compensating for the motion of the ultrasound probe, Signed and Sealed this
Third Day of November, 2020

Andrei Iancu
*Director of the United States Patent and Trademark Office* wherein the controller is further configured to compensate for the motion of the ultrasound probe, at least in part by adjusting how the ultrasound probe performs the acquisition task by continuing imaging, using beam steering, a same portion of a subject as was being imaged prior to the motion of the ultrasound probe.--

Claim 30, Column 34, Line 45:
"30. The computer-readable storage device of claim 23,"
Should be replaced with:
--30. The ultrasound apparatus of claim 23,--